US008388872B2

(12) United States Patent
Chopra et al.

(10) Patent No.: US 8,388,872 B2
(45) Date of Patent: *Mar. 5, 2013

(54) PHOTOCHROMIC MATERIALS HAVING EXTENDED PI-CONJUGATED SYSTEMS AND COMPOSITIONS AND ARTICLES INCLUDING THE SAME

(75) Inventors: Anu Chopra, Pittsburgh, PA (US); Jun Deng, Murrysville, PA (US); Beon-Kyu Kim, Gibsonia, PA (US); David B. Knowles, Apollo, PA (US); Frank F. Molock, Jr., Orange Park, FL (US); Victor A. Montes, Monroeville, PA (US); Stephen D. Straight, Austin, TX (US); Wenjing Xiao, Murrysville, PA (US); Huayun Yu, Monroeville, PA (US)

(73) Assignee: Transitions Optical, Inc., Pinellas Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/400,734

(22) Filed: Feb. 21, 2012

(65) Prior Publication Data

US 2012/0145975 A1 Jun. 14, 2012

Related U.S. Application Data

(60) Division of application No. 12/873,735, filed on Sep. 1, 2010, now Pat. No. 8,147,725, which is a continuation-in-part of application No. 12/136,339, filed on Jun. 10, 2008, now abandoned, which is a division of application No. 11/102,279, filed on Apr. 8, 2005, now abandoned.

(51) Int. Cl.
G02B 5/23 (2006.01)
C07D 311/78 (2006.01)
C07D 311/94 (2006.01)

(52) U.S. Cl. ............ 252/586; 252/582; 428/411.1; 544/31; 544/99; 544/338; 544/375; 544/401; 546/167; 546/196; 549/381; 549/382

(58) Field of Classification Search .............. 252/582, 252/586; 428/411.1; 544/31, 99, 338, 375, 544/401; 546/167, 196; 549/381, 382
See application file for complete search history.

(56) References Cited

U.S. PATENT DOCUMENTS

| | | |
|---|---|---|
| 3,933,509 A | 1/1976 | Noguchi et al. |
| 4,929,693 A | 5/1990 | Akashi et al. |
| 5,166,345 A | 11/1992 | Akashi et al. |
| 5,236,958 A | 8/1993 | Miyashita |
| 5,252,742 A | 10/1993 | Miyashita |
| 5,359,085 A | 10/1994 | Iwamoto et al. |
| 5,458,814 A | 10/1995 | Kumar et al. |
| 5,645,767 A | 7/1997 | Van Gemert |
| 5,651,923 A | 7/1997 | Kumar et al. |
| 5,821,287 A | 10/1998 | Hu et al. |
| 5,952,515 A | 9/1999 | Melzig et al. |
| 6,025,026 A | 2/2000 | Smith et al. |
| 6,036,890 A | 3/2000 | Melzig et al. |
| 6,068,797 A | 5/2000 | Hunt |
| 6,113,814 A | 9/2000 | Gemert et al. |
| 6,146,554 A | 11/2000 | Melzig et al. |
| 6,150,430 A | 11/2000 | Walters et al. |
| 6,190,580 B1 | 2/2001 | Melzig et al. |
| 6,296,785 B1 | 10/2001 | Nelson et al. |
| 6,469,076 B1 | 10/2002 | Momoda et al. |
| 6,555,028 B2 | 4/2003 | Walters et al. |
| 6,630,597 B1 | 10/2003 | Lin et al. |
| 6,723,859 B2 | 4/2004 | Kawabata et al. |
| 6,747,145 B2 | 6/2004 | Zhao et al. |
| 7,556,750 B2 | 7/2009 | Xiao et al. |
| 2003/0141490 A1 | 7/2003 | Walters et al. |
| 2003/0165686 A1 | 9/2003 | Blackburn et al. |
| 2004/0185255 A1 | 9/2004 | Walters |
| 2004/0186241 A1 | 9/2004 | Van Gemert |
| 2005/0258408 A1 | 11/2005 | Molock et al. |
| 2006/0226401 A1 | 10/2006 | Xiao et al. |
| 2006/0227287 A1 | 10/2006 | Molock et al. |
| 2006/0228557 A1 | 10/2006 | Kim et al. |
| 2008/0103301 A1 | 5/2008 | Chopra et al. |
| 2011/0108781 A1 | 5/2011 | Tomasulo |

FOREIGN PATENT DOCUMENTS

| | | |
|---|---|---|
| EP | 1 054 010 A1 | 5/2000 |
| EP | 1 184 379 A1 | 12/2000 |
| WO | WO 97/05213 | 2/1997 |
| WO | WO 98/28289 | 7/1998 |
| WO | WO 99/23071 | 5/1999 |
| WO | WO 2004/041961 | 5/2004 |
| WO | WO 2011/053615 A1 | 5/2011 |

Primary Examiner — Bijan Ahvazi
(74) Attorney, Agent, or Firm — Deborah M Altman; Frank P. Mallak

(57) ABSTRACT

The present invention provides a photochromic material which is an indeno-fused naphthopyran of structural formulas I or II, having a pi-conjugation extending group bonded to the 11-position of the indeno-fused naphthopyran, the pi-conjugation extending group having at least one pendent halo-substituted group bonded thereto. The pi-conjugation extending group extends the pi-conjugation system of said indeno-fused naphthopyran. The 13-position of the indeno-fused naphthopyran is substantially free of spiro-substituents. The invention further provides photochromic materials of specified structure, photochromic compositions, photochromic articles and optical elements that include the photochromic material.

11 Claims, 8 Drawing Sheets

PHOTOCHROMIC MATERIALS HAVING EXTENDED PI-CONJUGATED SYSTEMS AND COMPOSITIONS AND ARTICLES INCLUDING THE SAME

CROSS REFERENCE TO RELATED APPLICATIONS

This application is a division of U.S. application Ser. No. 12/873,735, filed Sep. 1, 2010, which is a continuation-in-part of U.S. application Ser. No. 12/136,339, filed Jun. 10, 2008, which is a division of U.S. patent application Ser. No. 11/102,279, filed Apr. 8, 2005, each of which is incorporated by reference herein in its entirety. The inventions claimed in this application were made as a result of activities undertaken within the scope of a joint research agreement between Transitions Optical, Inc. and Johnson & Johnson Vision Care, Inc. having an effective date of Apr. 1, 2003.

BACKGROUND

Various non-limiting embodiments disclosed herein relate to photochromic materials having an extended pi-conjugated system. Other non-limiting embodiments relate to photochromic compositions and articles, such as optical elements, incorporating the same.

Many conventional photochromic materials, such as indeno-fused naphthopyrans, can undergo a transformation in response to certain wavelengths of electromagnetic radiation (or "actinic radiation") from one form (or state) to another, with each form having a characteristic absorption spectrum. As used herein the term "actinic radiation" refers to electromagnetic radiation that is capable of causing a photochromic material to transform from one form or state to another. For example, many conventional photochromic materials are capable of transforming from a closed-form, corresponding to a "bleached" or "unactivated" state of the photochromic material, to an open-form, corresponding to a "colored" or "activated" state of the photochromic material, in response to actinic radiation, and reverting back to the closed-form in the absence of the actinic radiation in response to thermal energy. Photochromic compositions and articles that contain one or more photochromic materials, for example photochromic lenses for eyewear applications, may display clear and colored states that generally correspond to the states of the photochromic material(s) that they contain.

Typically, the amount of a photochromic material needed to achieve a desired optical effect when incorporated into a composition or article will depend, in part, on the amount of actinic radiation that the photochromic material absorbs on a per molecule basis. That is, the more actinic radiation that the photochromic material absorbs on a per molecule basis, the more likely (i.e., the higher the probability) the photochromic material will transform from the closed-form to the open-form. Photochromic compositions and articles that are made using photochromic materials having a relatively high molar absorption coefficient (or "extinction coefficient") for actinic radiation may generally be used in lower concentrations than photochromic materials having lower molar absorption coefficients, while still achieving the desired optical effect.

For some applications, the amount of photochromic material that can be incorporated into the article may be limited due to the physical dimensions of the article. Accordingly, the use of conventional photochromic materials that have a relatively low molar absorption coefficient in such articles may be impractical because the amount photochromic material needed to achieve the desired optical effects cannot be physically accommodated in the article. Further, in other applications, the size or solubility of the photochromic material itself may limit the amount of the photochromic material that can be incorporated into the article. Additionally, since photochromic materials may be expensive, in still other applications, the amount of photochromic material be used may be limited due to economic considerations.

Accordingly, for some applications, it may be advantageous to develop photochromic materials that can display hyperchromic absorption of actinic radiation, which may enable the use of lower concentrations of the photochromic material while still achieving the desired optical effects. As used herein, the term "hyperchromic absorption" refers to an increase in the absorption of electromagnetic radiation by a photochromic material having an extended pi-conjugated system on a per molecule basis as compared to a comparable photochromic material that does not have an extended pi-conjugated system.

Additionally, as mentioned above, typically the transformation between the closed-form and the open-form requires that the photochromic material be exposed to certain wavelengths of electromagnetic radiation. For many conventional photochromic materials, the wavelengths of electromagnetic radiation that may cause this transformation typically range from 320 nanometers ("nm") to 390 nm. Accordingly, conventional photochromic materials may not be optimal for use in applications that are shielded from a substantial amount of electromagnetic radiation in the range of 320 nm to 390 nm. For example, lenses for eyewear applications that are made using conventional photochromic materials may not reach their fully-colored state when used in an automobile. This is because a large portion of electromagnetic radiation in the range of 320 nm to 390 nm can be absorbed by the windshield of the automobile before it can be absorbed by the photochromic material(s) in the lenses. Therefore, for some applications, it may be advantageous to develop photochromic materials that can have a closed-form absorption spectrum for electromagnetic radiation that is shifted to longer wavelengths, that is "bathochromically shifted." As used herein the term "closed-form absorption spectrum" refers to the absorption spectrum of the photochromic material in the closed-form or unactivated state. For example, in applications involving behind the windshield use of photochromic materials, it may be advantageous if the closed-form absorption spectrum of the photochromic material were shifted such that the photochromic material may absorb sufficient electromagnetic radiation having a wavelength greater than 390 nm to permit the photochromic material to transform from the closed-form to an open-form.

BRIEF SUMMARY OF THE INVENTION

The present invention is directed to a photochromic material comprising an indeno-fused naphthopyran comprising a pi-conjugation extending group bonded to the 11-position of the indeno-fused naphthopyran, wherein the pi-conjugation extending group extends the pi-conjugation system of the indeno-fused naphthopyran. The pi-conjugation extending group has at least one pendent halo-substituted group bonded thereto, and the 13-position of the indeno-fused naphthopyran is substantially free of spiro-substituents.

The present invention further provides a photochromic material represented by graphic formulas I and II:

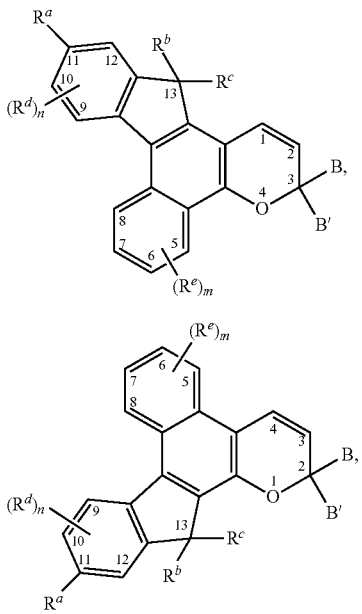

or a mixture thereof, wherein substituent groups $R^a$, $R^b$, $R^c$, $R^d$, $R^e$, B, and B', and m and n are as described herein below in the claims.

Also provided is a photochromic composition comprising the photochromic material described above incorporated into at least a portion of an organic material comprised of a polymeric material, an oligomeric material, a monomeric material or a mixture or combination thereof.

The present invention also is directed to a photochromic article and an optical element comprising the above-described photochromic material.

DETAILED DESCRIPTION

Figure 1:
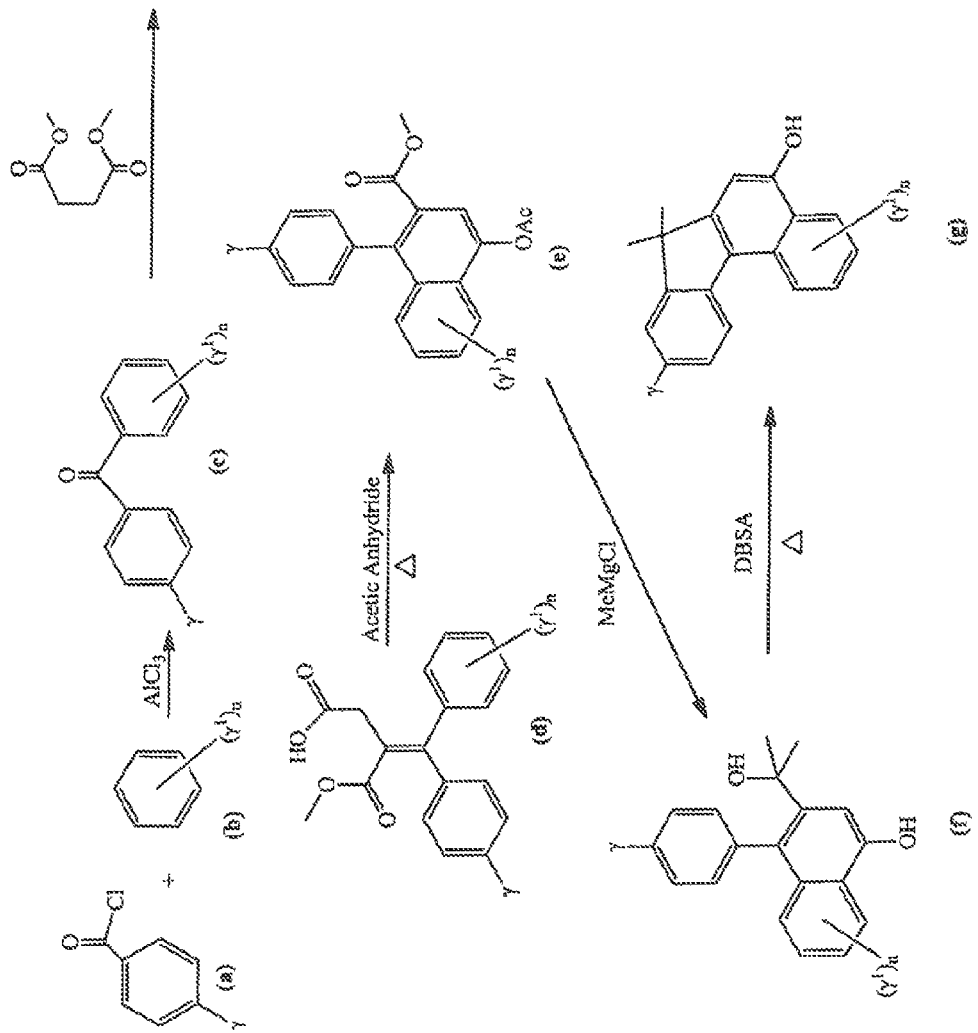
FIG. 1 is a representative schematic diagram of a reaction scheme for making an intermediate material that may be used in forming photochromic materials according to the present invention.

As used in this specification and the appended claims, the articles "a," "an," and "the" include plural referents unless expressly and unequivocally limited to one referent.

Additionally; for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Photochromic materials according to various non-limiting embodiments of the invention will now be discussed. As used herein, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation. As previously discussed, as used herein the term "actinic radiation" refers to electromagnetic radiation that is capable of causing a photochromic material transform from one form or state to another.

As previously mentioned, the present invention is directed to a photochromic material comprising an indeno-fused naphthopyran comprising a pi-conjugation extending group bonded to the 11-position of the indeno-fused naphthopyran, the pi-conjugation extending group having at least one pendent halo-substituted group bonded thereto. The pi-conjugation extending group serves to extend the pi-conjugation system of the indeno-fused naphthopyran. The 13-position of the indeno-fused naphthopyran is substantially free of spiro-substituents.

As used herein, the terms "10-position," "11-position," "12-position," "13-position," etc. refer to the 10-, 11-, 12- and 13-position, etc. of the ring atoms of the indeno-fused naphthopyran, respectively. For example, according to one non-limiting embodiment wherein the indeno-fused naphthopyran is an indeno[2',3':3,4]naphtho[1,2-b]pyran, the ring atoms of the indeno-fused naphthopyran are numbered as shown below in (I). According to another non-limiting embodiment wherein the indeno-fused naphthopyran is an indeno[1',2':4,3-b]naphtho[2,1-b]pyran, the ring atoms of the indeno-fused naphthopyran are numbered shown below in (II).

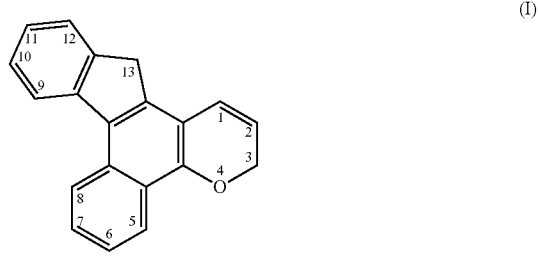

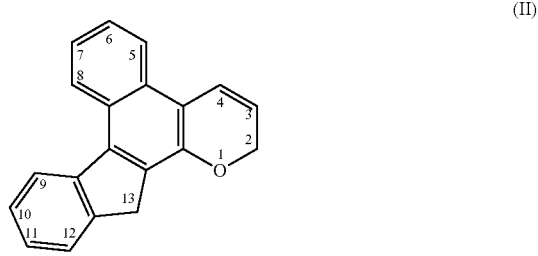

Further, according to various non-limiting embodiments disclosed herein, the indeno-fused naphthopyrans may have group(s) that can stabilize the open-form of the indeno-fused naphthopyran bonded to the pyran ring at an available position adjacent the oxygen atom (i.e., the 3-position in (I) above, or the 2-position in (II) above). For example, according to one non-limiting embodiment, the indeno-fused naphthopyrans may have a group that can extend the pi-conjugated system of the open-form of the indeno-fused naphthopyran bonded to the pyran ring adjacent the oxygen atom. Non-limiting examples of groups that may be bonded to the pyran ring as discussed above are described in more detail herein below with reference to B and B'.

Further, as discussed in more detail herein below, in addition to the group that extends the pi-conjugated system of the indeno-fused naphthopyran bonded at the 11-position of the indeno-fused naphthopyran, the photochromic materials according to various non-limiting embodiments disclosed may include additional groups bonded or fused at various positions on the indeno-fused naphthopyran other than the 11-position, provided that the 13-position of the indeno-fused naphthopyran is substantially free of spiro-substituents.

As used herein, the terms "group" or "groups" mean an arrangement of one or more atoms. As used herein, the phrase "group that extends the pi-conjugated system of the indeno-fused naphthopyran" means a group having at least one pi-bond (π-bond) in conjugation with the pi-conjugated system of the indeno-fused naphthopyran. It will be appreciated by those skilled in the art that in such system, the pi-electrons in the pi-conjugated system of the indeno-fused naphthopyran can be de-localized over the pi-system of the indeno-fused naphthopyran and the group having at least one pi-bond in conjugation with the pi-conjugated system of the indeno-fused naphthopyran. Conjugated bond systems may be represented by an arrangement of at least two double or triple bonds separated by one single bond, that is a system containing alternating double (or triple) bonds and single bonds, wherein the system contains at least two double (or triple) bonds. Non-limiting examples of groups that may extend the pi-conjugated system of the indeno-fused naphthopyran according to various non-limiting embodiments disclosed herein are set forth below in detail.

As previously discussed, the more actinic radiation that a photochromic material absorbs on a per molecule basis, the more likely the photochromic material will be to make the transformation from the closed-form to the open-form. Further, as previously discussed, photochromic materials that absorb more actinic radiation on a per molecule basis may generally be used in lower concentrations than those that absorb less actinic radiation on a per molecule basis, while still achieving the desired optical effects.

Although not meant to be limiting herein, it has been observed by the inventors that the indeno-fused naphthopyrans that comprise a group that extends the pi-conjugated system of the indeno-fused naphthopyran bonded at the 11-position thereof which has at least one pendant halo-substituted group bonded thereto according to certain non-limiting embodiments of the present invention may absorb more actinic radiation on a per molecule basis than a comparable indeno-fused naphthopyran without such a group that extends the pi-conjugated system of the comparable indeno-fused naphthopyran bonded at the 11-position thereof. That is, the indeno-fused naphthopyrans according to the present invention may display hyperchromic absorption of actinic radiation. As discussed above, as used herein the term "hyperchromic absorption" refers to an increase in the absorption of electromagnetic radiation by a photochromic material having an extended pi-conjugated system on a per molecule basis as compared to a comparable photochromic material that does not have an extended pi-conjugated system. Thus, while not meant to be limiting herein, it is contemplated that the indeno-fused naphthopyrans according to certain non-limiting embodiments disclosed herein may be advantageously employed in many applications, including applications wherein it may be necessary or desirable to limit the amount of the photochromic material employed.

The amount of radiation absorbed by a material (or the "absorbance" of the material) can be determined using a spectrophotometer by exposing the material to incident radiation having a particular wavelength and intensity and comparing the intensity of radiation transmitted by the material to that of the incident radiation. For each wavelength tested, the absorbance ("A") of the material is given by the following equation:

$$A = \log I_0/I$$

wherein "$I_0$" is the intensity of the incident radiation and "I" is the intensity of the transmitted radiation. An absorption spectrum for the material can be obtained by plotting the absorbance of a material vs. wavelength. By comparing the absorption spectrum of photochromic materials that were tested under the same conditions, that is using the same concentration and path length for electromagnetic radiation passing through the sample (e.g., the same cell length or sample thickness), an increase in the absorbance of one of the materials at a given wavelength can be seen as an increase in the intensity of the spectral peak for that material at that wavelength.

Another indication of the amount of radiation a material can absorb is the extinction coefficient of the material. The extinction coefficient ("$\epsilon$") of a material is related to the absorbance of the material by the following equation:

$$\epsilon = A/(c \times l)$$

wherein "A" is the absorbance of the material at a particular wavelength, "c" is the concentration of the material in moles per liter (mol/L) and "l" is the path length (or cell thickness) in centimeters. Further, by plotting the extinction coefficient vs. wavelength and integrating over a range of wavelengths (e.g., $=\int \epsilon(\lambda) d\lambda$) it is possible to obtain an "integrated extinction coefficient" for the material. Generally speaking, the higher the integrated extinction coefficient of a material, the more radiation the material will absorb on a per molecule basis.

The photochromic materials according various non-limiting embodiments disclosed herein may have an integrated extinction coefficient greater than $1.0 \times 10^6$ nm/(mol×cm) or (nm×mol$^{-1}$×cm$^{-1}$) as determined by integration of a plot of extinction coefficient of the photochromic material vs. wavelength over a range of wavelengths ranging from 320 nm to 420 nm, inclusive. Further, the photochromic materials according to various non-limiting embodiments disclosed herein may have an integrated extinction coefficient of at least $1.1 \times 10^6$ nm×mol$^{-1}$×cm$^{-1}$ or at least $1.3 \times 10^6$ nm×mol$^{-1}$×cm$^{-1}$ as determined by integration of a plot of extinction coefficient of the photochromic material vs. wavelength over a range of wavelengths ranging from 320 nm to 420 nm, inclusive. For example, according to various non-limiting embodiments, the photochromic material may have an integrated extinction coefficient ranging from $1.1 \times 10^6$ to $4.0 \times 10^6$ nm×mol$^{-1}$×cm$^{-1}$ (or greater) as determined by integration of a plot of extinction coefficient of the photochromic material vs. wavelength over a range of wavelengths ranging from 320 nm to 420 nm, inclusive. However, as indicated above, generally speaking the higher the integrated extinction coefficient of a photochromic material, the more radiation the photochromic material will absorb on a per molecule basis. Accordingly, other non-limiting embodiments disclosed herein contemplate photochromic materials having an integrated extinction coefficient greater than $4.0 \times 10^6$ nm×mol$^{-1}$×cm$^{-1}$.

As previously discussed, for many conventional photochromic materials, the wavelengths of electromagnetic radiation required to cause the material to transformation from a closed-form (or unactivated state) to an open-form (or activated state) may range from 320 nm to 390 nm. Thus, conventional photochromic materials may not achieve their fully-colored state when used in applications that are shielded from a substantial amount of electromagnetic radiation in the range of 320 nm to 390 nm. Although not meant to be limiting herein, it has been observed by the inventors that indeno-fused naphthopyrans comprising a group that extends the pi-conjugated system of the indeno-fused naphthopyran at the 11-position thereof according to certain non-limiting embodiments disclosed herein may have a closed-form absorption spectrum for electromagnetic radiation that is bathochromically shifted as compared to a closed-form absorption spectrum for electromagnetic radiation of a comparable indeno-fused naphthopyran without the group that extends the pi-conjugated system of the comparable indeno-fused naphthopyran bonded at the 11-position thereof. As discussed above, as used herein the term "closed-form absorption spectrum" refers to the absorption spectrum of the photochromic material in the closed-form or unactivated state.

In the present invention, the indeno-fused naphthopyran comprises a pi-conjugation extending group bonded to the 11-position of the indeno-fused naphthopyran wherein the pi-conjugation extending group has at least one pendent halo-substituted group bonded thereto. The pi-conjugation extending group can be a group represented by —C(R$_{30}$)═C(R$_{31}$)(R$_{32}$) or —C≡C—R$_{33}$, wherein R$_{30}$, R$_{31}$ and R$_{32}$ are each independently, amino, dialkyl amino, diaryl amino, acyloxy, acylamino, a substituted or unsubstituted C$_1$-C$_{20}$ alkyl, a substituted or unsubstituted C$_2$-C$_{20}$ alkenyl, a substituted or unsubstituted C$_2$-C$_{20}$ alkynyl, halogen, hydrogen, hydroxy, oxygen, a polyol residue, a substituted or unsubstituted phenoxy, a substituted or unsubstituted benzyloxy, a substituted or unsubstituted alkoxy, a substituted or unsubstituted oxyalkoxy, alkylamino, mercapto, alkylthio, a substituted or unsubstituted aryl, a substituted or unsubstituted heteroaryl, a substituted or unsubstituted heterocyclic group, provided that at least one of R$_{30}$, R$_{31}$ and R$_{32}$ is the pendent halo-substituted group, and R$_{33}$ is the pendent halo-substituted group.

Additionally, the pendent halo-substituted group of the pi-conjugation extending group can be selected from halo-substituted(C$_1$-C$_{10}$)alkyl, halo-substituted(C$_2$-C$_{10}$)alkenyl, halo-substituted(C$_2$-C$_{10}$)alkynyl, halo-substituted(C$_1$-C$_{10}$)alkoxy and halo-substituted(C$_3$-C$_{10}$)cycloalkyl, wherein each halo group of each pendent halo-substituted group independently is selected from fluorine, chlorine, bromine or iodine.

In a particular embodiment of the present invention, the pi-conjugation extending group having at least one pendent halo-substituted group bonded thereto can be selected from substituted or unsubstituted aryl, and substituted or unsubstituted heteroaryl, wherein the substituted aryl and said substituted heteroaryl are in each case independently substituted with at least one member selected from substituted or unsubstituted alkyl, substituted or unsubstituted alkoxy, substituted or unsubstituted oxyalkoxy, amide, substituted or unsubstituted amino, substituted or unsubstituted aryl, substituted or unsubstituted heteroaryl, azide, carbonyl, carboxy, ester, ether, halogen, hydroxy, polyol residue, substituted or unsubstituted phenoxy, substituted or unsubstituted benzyloxy, cyano, nitro, sulfonyl, thiol, and substituted or unsubstituted heterocyclic group. In such an embodiment, if the aryl group or the heteroaryl group comprises more than one substituent, each substituent may be chosen independent of the others.

The photochromic material as described above displays hyperchromic absorption of electromagnetic radiation having a wavelength from 320 nm to 420 nm as compared to a comparative photochromic material comprising a comparable indeno-fused naphthopyran that is substantially free of a pi-conjugation extending group bonded to the 11-position which has at least one pendent halo-substituted group bonded thereto.

The present invention also is directed to a photochromic article comprising a substrate and any of the previously described photochromic materials connected to at least a portion of the substrate. The substrate can comprise a polymeric material and the photochromic material can be incorporated into at least a portion of the polymeric material. The photochromic material can be blended with at least a portion of the polymeric material, or the photochromic material can be bonded to at least a portion of the polymeric material, and/or the photochromic material can be imbibed into at least a portion of the polymeric material.

Such photochromic articles can include an optical element, for example, an ophthalmic element, a display element, a window, a mirror and a liquid crystal cell element. The ophthalmic element can include at least one of a corrective lens, a non-corrective lens, a magnifying lens, a protective lens, a visor, goggles, or a lens for an optical instrument.

Additionally, the present invention is directed to a photochromic material represented by graphic formulas I and II:

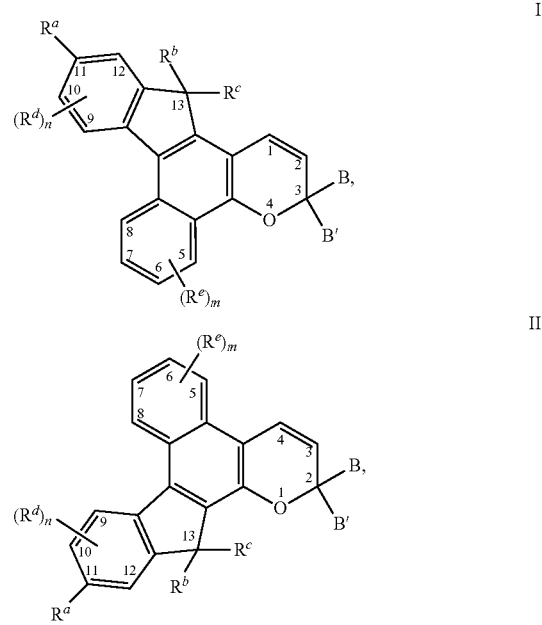

or a mixture thereof, wherein:
(i) R$^a$ is a pi-conjugation extending group bonded to the 11-position of the indeno-fused naphthopyran, said pi-conjugation extending group having at least one pendent halo-substituted group bonded thereto, the pi-conjugation extending group extending the pi-conjugation system of the indeno-fused naphthopyran, provided the 13-position of said indeno-fused naphthopyran is substantially free of spiro-substituents; wherein said pi-conjugation extending group is a group represented by —C($R_{30}$)=C($R_{31}$)($R_{32}$) or —C≡C—$R_{33}$, wherein $R_{30}$, $R_{31}$ and $R_{32}$ are each independently, amino, dialkyl amino, diaryl amino, acyloxy, acylamino, a substituted or unsubstituted $C_1$-$C_{20}$ alkyl, a substituted or unsubstituted $C_2$-$C_{20}$ alkenyl, a substituted or unsubstituted $C_2$-$C_{20}$ alkynyl, halogen, hydrogen, hydroxy, oxygen, a polyol residue, a substituted or unsubstituted phenoxy, a substituted or unsubstituted benzyloxy, a substituted or unsubstituted alkoxy, a substituted or unsubstituted oxyalkoxy, alkylamino, mercapto, alkylthio, a substituted or unsubstituted aryl, a substituted or unsubstituted heteroaryl, a substituted or unsubstituted heterocyclic group, provided that at least one of $R_{30}$, $R_{31}$ and $R_{32}$ is a pendent halo-substituted group, and $R_{33}$ is the pendent halo-substituted group; or the pi-conjugation extending group is selected from a substituted or unsubstituted aryl; and a substituted or unsubstituted heteroaryl;
(ii) n ranges from 0 to 3;
(iii) m ranges from 0 to 4;
(iv) each $R^d$ and $R^e$ is independently chosen for each occurrence from:
a reactive substituent; a compatiblizing substituent; hydrogen; $C_1$-$C_6$ alkyl; halo; $C_3$-$C_7$ cycloalkyl; a substituted or unsubstituted phenyl, said phenyl substituents being $C_1$-$C_6$ alkyl or $C_1$-$C_6$ alkoxy; —$OR^{10}$ or —OC(=O)$R^{10}$ wherein $R^{10}$ is S, hydrogen, amine, $C_1$-$C_6$ alkyl, phenyl ($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl or mono($C_1$-$C_4$)alkyl substituted $C_3$-$C_7$ cycloalkyl; a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_t$— or —[O—(CH$_2$)$_t$]$_k$—, wherein t ranges from 2 to 6, and k ranges from 1 to 50, and wherein the substituent is connected to an aryl group on another photochromic material; —N($R^{11}$)$R^{12}$, wherein $R^{11}$ and $R^{12}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, or $R^{11}$ and $R^{12}$ come together with the nitrogen atom to form a $C_3$-$C_{20}$ hetero-bicycloalkyl ring or a $C_4$-$C_{20}$ hetero-tricycloalkyl ring; a nitrogen containing ring represented by:

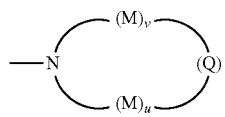

wherein each -M- is independently chosen for each occurrence from —CH$_2$—, —CH($R^{13}$)—, —C($R^{13}$)$_2$—, —CH(aryl)-, —C(aryl)$_2$- and —C($R^{13}$)(aryl)-, and -Q- is -M-, —O—, —S—, —S(O)—, —SO$_2$—, —NH—, —N($R^{13}$)— or —N(aryl)-, wherein each $R^{13}$ is independently $C_1$-$C_6$ alkyl, each (aryl) is independently phenyl or naphthyl, u ranges from 1 to 3, and v ranges from 0 to 3, provided that if v is 0, -Q- is -M-; a group represented by:

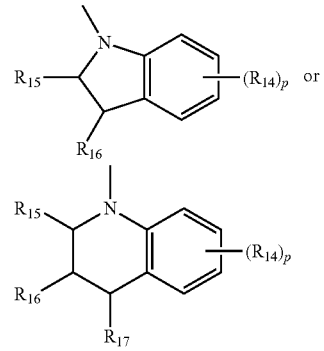

wherein each $R^{15}$, $R^{16}$ and $R^{17}$ is independently hydrogen, $C_1$-$C_6$ alkyl, phenyl or naphthyl, or $R^{15}$ and $R^{16}$ together form a ring of 5 to 8 carbon atoms, each $R^{14}$ is independently $C_1$-$C_6$ alkyl, $C_1$-$C_6$ alkoxy, halo, and p ranges from 0 to 3; and a substituted or unsubstituted $C_4$-$C_{18}$ spirobicyclic amine or a substituted or unsubstituted $C_4$-$C_{18}$ spirotricyclic amine, wherein said substituents are independently aryl, $C_1$-$C_6$ alkyl, $C_1$-$C_6$ alkoxy or phenyl($C_1$-$C_6$)alkyl; or
an $R^e$ group in the 6-position and an $R^e$ group in the 7-position together form a group represented by:

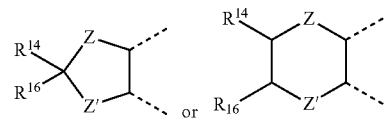

wherein each Z and Z' is independently oxygen or the group —$NR^{11}$— wherein $R^{11}$, $R^{14}$ and $R^{16}$ are as set forth above;
(v) $R^b$ and $R^c$ are each independently:
a reactive substituent; a compatiblizing substituent; hydrogen; hydroxy; $C_1$-$C_6$ alkyl; $C_3$-$C_7$ cycloalkyl; allyl; a substituted or unsubstituted phenyl or benzyl, wherein each of said phenyl and benzyl substituents is independently $C_1$-$C_6$ alkyl or $C_1$-$C_6$ alkoxy; halo; a substituted or unsubstituted amino; —C(O)$R^9$ wherein $R^9$ is hydrogen, hydroxy, $C_1$-$C_6$ alkyl, $C_1$-$C_6$ alkoxy, an unsubstituted, mono- or di-substituted phenyl or naphthyl wherein each of said substituents is independently $C_1$-$C_6$ alkyl or $C_1$-$C_6$ alkoxy, phenoxy, mono- or di-($C_1$-$C_6$)alkyl substituted phenoxy, mono- or di-($C_1$-$C_6$) alkoxy substituted phenoxy, amino, mono- or di-($C_1$-$C_6$) alkylamino, phenylamino, mono- or di-($C_1$-$C_6$)alkyl substituted phenylamino or mono- or di-($C_1$-$C_6$)alkoxy substituted phenylamino; —$OR^{18}$ wherein $R^{18}$ is $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ haloalkyl, allyl or —CH($R^{19}$)T wherein $R^{19}$ is hydrogen or $C_1$-$C_3$ alkyl, T is CN, CF$_3$ or COOR$^{20}$ wherein $R^{20}$ is hydrogen or $C_1$-$C_3$ alkyl, or wherein $R^{18}$ is —C(=O)U wherein U is hydrogen, $C_1$-$C_6$ alkyl, $C_1$-$C_6$ alkoxy, an unsubstituted, mono- or di-substituted phenyl or naphthyl, wherein each of said substituents are independently $C_1$-$C_6$ alkyl or $C_1$-$C_6$ alkoxy, phenoxy, mono- or di-($C_1$-$C_6$)alkyl substituted phenoxy, mono- or di-($C_1$-$C_6$)alkoxy substituted phenoxy, amino, mono- or di-($C_1$-$C_6$)alkylamino, phenylamino, mono- or di-($C_1$-$C_6$)alkyl substituted phenylamino or mono- or di-($C_1$-$C_6$)alkoxy substituted phenylamino; and a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_t$— or —[O—($CH_2$)$_t$]$_k$—, wherein t ranges from 2 to 6 and k ranges from 1 to 50, and wherein the substituent is connected to an aryl group on another photochromic material; or $R^b$ and $R^c$ together form an oxo group; provided that the 13-position of said indeno-fused naphthopyran is substantially free of spiro-substituents; and (vi) B and B' are each independently:

an aryl group that is mono-substituted with a reactive substituent or a compatiblizing substituent; an unsubstituted, mono-, di-, tri- or tetra-substituted aryl group; 9-julolidinyl; an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl; wherein the aryl and heteroaromatic substituents are each independently:

hydroxy, aryl, mono- or di-($C_1$-$C_{12}$)alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, halogen, or —C(=O)$R^{21}$ wherein $R^{21}$ is –O$R^{22}$, —N($R^{23}$)$R^{24}$, piperidino or morpholino, wherein $R^{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{23}$ and $R^{24}$ are each independently $C_1$-$C_6$ alkyl, $C_5$-$C_7$ cycloalkyl or a substituted or unsubstituted phenyl, said phenyl substituents independently being $C_1$-$C_6$ alkyl or $C_1$-$C_6$ alkoxy;

an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, said substituents being $C_1$-$C_{12}$ alkyl, $C_1$-$C_{12}$ alkoxy, phenyl or halogen; a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_t$— or —[O—($CH_2$)$_t$]$_k$—, wherein t ranges form 2 to 6 and k ranges from 1 to 50, and wherein the substituent is connected to an aryl group on another photochromic material; a group represented by:

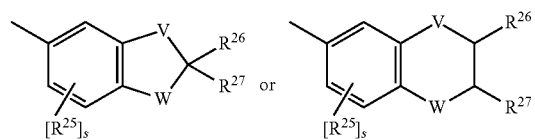

wherein V is —$CH_2$— or —O—, W is oxygen or substituted nitrogen, provided that when W is substituted nitrogen, V is —$CH_2$—, the substituted nitrogen substituents being hydrogen, $C_1$-$C_{12}$ alkyl or $C_1$-$C_{12}$ acyl, each $R^{25}$ independently being $C_{12}$ alkyl, $C_1$-$C_{12}$ alkoxy, hydroxy or halogen, $R^{26}$ and $R^{27}$ are each independently hydrogen or $C_1$-$C_{12}$ alkyl, and s ranges from 0 to 2; or a group represented by:

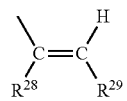

wherein $R^{28}$ is hydrogen or $C_1$-$C_{12}$ alkyl, and $R^{20}$ is an unsubstituted, mono- or di-substituted naphthyl, phenyl, furanyl or thienyl, said substituents being $C_1$-$C_{12}$ alkyl, $C_1$-$C_{12}$ alkoxy or halogen; or B and B' taken together form a fluoren-9-ylidene or mono- or di-substituted fluoren-9-ylidene, each of said fluoren-9-ylidene substituents independently being $C_1$-$C_{12}$ alkyl, $C_1$-$C_{12}$ alkoxy or halogen.

Further, the photochromic material described herein can comprise at least one of a reactive substituent and a compatiblizing substituent, each of the reactive substituent or compatiblizing substituent being independently represented by one of:

| | | |
|---|---|---|
| -A'-D-E-G-J; | -G-E-G-J; | -D-E-G-J; |
| -A'-D-J; | -D-G-J; | -D-J; |
| -A'-G-J; | -G-J; and | -A'-J; | wherein:

(i) each -A'- is independently —O—, —C(=O)—, —$CH_2$—, —OC(=O)— or —NHC(=O)—, provided that if -A'- is —O—, -A'- forms at least one bond with -J;

(ii) each -D- is independently:

(a) a diamine residue or a derivative thereof, the diamine residue being an aliphatic diamine residue, a cyclo aliphatic diamine residue, a diazacycloalkane residue, an azacyclo aliphatic amine residue, a diazacrown ether residue or an aromatic diamine residue, wherein a first amino nitrogen of the diamine residue forms a bond with -A'-, the group that extends the pi-conjugated system of the indeno-fused naphthopyran bonded at the 11-position thereof, or a substituent or an available position on the indeno-fused naphthopyran, and a second amino nitrogen of the diamine residue forms a bond with -E-, -G- or -J; or (b) an amino alcohol residue or a derivative thereof, the amino alcohol residue being an aliphatic amino alcohol residue, a cyclo aliphatic amino alcohol residue, an azacyclo aliphatic alcohol residue, a diazacyclo aliphatic alcohol residue or an aromatic amino alcohol residue, wherein an amino nitrogen of the amino alcohol residue forms a bond with -A'-, the group that extends the pi-conjugated system of the indeno-fused naphthopyran bonded at the 11-position thereof, or a substituent or an available position on the indeno-fused naphthopyran, and an alcohol oxygen of said amino alcohol residue forms a bond with -E-, -G- or -J, or the amino nitrogen of the amino alcohol residue forms a bond with -E-, -G- or -J, and the alcohol oxygen of the amino alcohol residue forms a bond with -A'-, the group that extends the pi-conjugated system of the indeno-fused naphthopyran bonded at the 11-position thereof, or a substituent or an available position on the indeno-fused naphthopyran;

(iii) each -E- is independently a dicarboxylic acid residue or a derivative thereof, said dicarboxylic acid residue being an aliphatic dicarboxylic acid residue, a cycloaliphatic dicarboxylic acid residue or an aromatic dicarboxylic acid residue, wherein a first carbonyl group of the dicarboxylic acid residue forms a bond with -G- or -D-, and a second carbonyl group of the dicarboxylic acid residue forms a bond with -G-;

(iv) each -G- is independently:
(a) —[$(OC_2H_4)_x(OC_3H_6)_y(OC_4-H_8)_z$]—O—, wherein x, y and z are each independently chosen and range from 0 to 50, and a sum of x, y, and z ranges from 1 to 50;
(b) a polyol residue or a derivative thereof, the polyol residue being an aliphatic polyol residue, a cyclo aliphatic polyol residue or an aromatic polyol residue, wherein a first polyol oxygen of said polyol residue forms a bond with -A'-, -D-, -E-, the group that extends the pi-conjugated system of the indeno-fused naphthopyran bonded at the 11-position thereof, or a substituent or an available position on the indeno-fused naphthopyran, and a second polyol oxygen of said polyol forms a bond with -E- or -J; or
(c) a combination thereof, wherein the first polyol oxygen of the polyol residue forms a bond with a group —[$(OC_2H_4)_x(OC_3H_6)_y(OC_4H_8)_z$]— and the second polyol oxygen forms a bond with, -E- or -J; and (v) each -J is independently:
(a) a group —K, wherein —K is —$CH_2COOH$, —$CH(CH_3)COOH$, —$C(O)(CH_2)_wCOOH$, —$C_6H_4SO_3H$, —$C_5H_{10}SO_3H$, —$C_4H_8SO_3H$, —$C_3H_6SO_3H$, $C_2H_4SO_3H$ or —$SO_3H$, wherein w ranges from 1 to 18;
(b) hydrogen, provided that if -J is hydrogen, -J is bonded to an oxygen of -D- or G-, or a nitrogen of -D-; or
(c) a group -L or residue thereof, wherein -L is acryl, methacryl, crotyl, 2-(methacryloxy)ethylcarbamyl, 2-(methacryloxy)ethoxycarbonyl, 4-vinylphenyl, vinyl, 1-chlorovinyl or epoxy.

At least one of an $R^e$ group at the 6-position, an $R^e$ group at the 7-position, B, B', $R^b$, $R^c$ and $R^a$ comprises a reactive substituent.

In a particular embodiment of the present invention, the photochromic material can be represented by graphic formula I wherein:

(i) each of an $R^e$ group at the 7-position and an $R^e$ group at the 6-position is independently —$OR^{10}$ wherein $R^{10}$ is $C_1$-$C_6$ alkyl, a substituted or unsubstituted phenyl, said phenyl substituents being $C_1$-$C_6$ alkyl or $C_1$-$C_6$ alkoxy, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl or mono($C_1$-$C_4$)alkyl substituted $C_3$-$C_7$ cycloalkyl; —$N(R^{11})R^{12}$ wherein $R^{11}$ and $R^{12}$ are each independently hydrogen, $C_1$-$C_6$ alkyl, $C_1$-$C_6$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl; a nitrogen containing ring represented by:

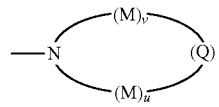

wherein each -M- is independently chosen for each occurrence from —$CH_2$—, —$CH(R^{13})$—, —$C(R^{13})_2$—, —CH(aryl)-, —$C(aryl)_2$- and —$C(R^{13})(aryl)$-, and -Q- is -M-, —O—, —S—, —NH—, —$N(R^{13})$— or —N(aryl)-, wherein each $R^{13}$ is independently $C_1$-$C_6$ alkyl, each (aryl) is independently phenyl or naphthyl, u ranges from 1 to 3, and v ranges from 0 to 3, provided that if v is 0, -Q- is -M-; or a reactive substituent or a compatiblizing substituent, provided that the reactive or compatiblizing substituent comprises a linking group comprising an aliphatic amino alcohol residue, a cyclo aliphatic amino alcohol residue, an azacyclo aliphatic alcohol residue, a diazacyclo aliphatic alcohol residue, a diamine residue, an aliphatic diamine residue, a cyclo aliphatic diamine residue, a diazacycloalkane residue, an azacyclo aliphatic amine residue, an oxyalkoxy group, an aliphatic polyol residue or a cyclo aliphatic polyol residue that forms a bond with the indeno[2',3':3,4]naphtho[1,2-b]pyran at the 6-position or the 7-position; or (ii) an $R^e$ group in the 6-position and an $R^e$ group in the 7-position of the indeno[2',3':3,4]naphtho[1,2-b]pyran together form a group represented by:

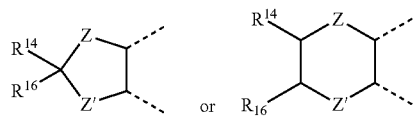

wherein Z and Z' are each independently oxygen or —$NR^{11}$—, wherein $R^{11}$ is as set forth above in (i).

For example, the photochromic material can be chosen from:
(i) 3,3-di(4-methoxyphenyl)-6,7-dimethoxy-11-(4-trifluoromethyl)phenyl-13,13-dimethyl-3H,13H-indeno[2',3':3,4]naphtho[1,2-b]pyran;
(ii) 3,3-di(4-methoxyphenyl)-6,7-dimethoxy-11-(3,5-bis(trifluoromethyl)phenyl)-13,13-dimethyl-3H,13H-indeno[2',3':3,4]naphtho[1,2-b]pyran;
(iii) 3,3-di(4-methoxyphenyl)-6,7-dimethoxy-11-(2-trifluoromethyl)phenyl-13,13-diethyl-3H,13H-indeno[2',3':3,4]naphtho[1,2-b]pyran;

(iv) 3,3-di-(4-methoxyphenyl)-6-methoxy-7-piperidino-11-(4-trifluoromethyl)phenyl-13,13-dimethyl-3H,13H-indeno[2',3':3,4]naphtho[1,2-b]pyran;
(v) 3-(4-methoxyphenyl)-3-(4-morpholinophenyl)-6,7-dimethoxy-11-(4-trifluoromethyl)phenyl-13,13-dimethyl-3H,13H-indeno[2',3':3,4]naphtho[1,2-b]pyran;
(vi) 3-(4-methoxyphenyl)-3-(4-morpholinophenyl)-6-methoxy-7-piperidino-11-(4-trifluoromethyl)phenyl-13,13-dimethyl-3H,13H-indeno[2',3':3,4]naphtho[1,2-b]pyran;
(vii) 3-(4-methoxyphenyl)-3-(4-morpholinophenyl)-6-methoxy-7-morpholino-11-(4-trifluoromethyl)phenyl-13,13-dimethyl-3H,13H-indeno[2',3':3,4]naphtho[1,2-b]pyran;
(viii) 3,3-di(4-hydroxyphenyl)-6,7-dimethoxy-11-(3,5-bis(trifluoromethyl)phenyl)-13,13-dimethyl-3H,13H-indeno[2',3':3,4]naphtho[1,2-b]pyran;
(ix) 3,3-di-(4-methoxyphenyl-6-methoxy-7-morpholino-11-(4-trifluoromethyl)phenyl-13,13-dimethyl-3H,13H-indeno[2',3':3,4]naphtho[1,2-b]pyran;
(x) 3,3-bis(4-methoxyphenyl)-6,7-dimethoxy-11-(2-trifluoromethyl)phenyl-13,13-dimethyl-3H,13H-indeno[2',3':3,4]naphtho[1,2-b]pyran;
(xi) 3,3-bis(4-methoxyphenyl)-6-methoxy-7-piperidino-11-(2-trifluoromethyl)phenyl-13,13-dimethyl-3H,13H-indeno[2',3':3,4]naphtho[1,2-b]pyran;
(xii) 3-phenyl-3'-(4-morpholinophenyl)-11-(4-trifluoromethyl)phenyl-13,13-dimethyl-3H,13H-indeno[2',3':3,4]naphtho[1,2-b]pyran;
(xiii) 3-(4-morpholinophenyl)-3-phenyl-11-(2-trifluoromethyl)-phenyl-13,13-dimethyl-3H,13H-indeno[2',3':3,4]naphtho[1,2-b]pyran;
(xiv) 3-(4-butoxyphenyl)-3-(4-methoxyphenyl)-6,7-dimethoxy-11-(3-(trifluoromethyl)pyridin-2-yl)-13,13-dimethyl-3H,13H-indeno[2',3':3,4]naphtho[1,2-b]pyran
(xv) and mixtures thereof.

Also, where the photochromic material comprising the group that extends the pi-conjugated system bonded at the 11-position thereof comprises an additional photochromic material that is linked thereto, the additional photochromic material may be linked to the photochromic material comprising the group that extends the pi-conjugated system bonded at the 11-position thereof by an insulating group. As used herein, the term "insulating group" means a group having at least two consecutive sigma ($\sigma$) bonds that separate the pi-conjugated systems of the photochromic materials. For example, the insulating group may be the alkyl portion of a piperazino group or the alkyl portion of an oxyalkoxy group.

Still further, and as discussed in more detail below, according to various non-limiting embodiments, the group that extends the pi-conjugated system of the indeno-fused naphthopyran bonded at the 11-position also may comprise a reactive substituent or a compatiblizing substituent. As used herein the term "reactive substituent" means an arrangement of atoms, wherein a portion of the arrangement comprises a reactive moiety or a residue thereof. As used herein, the term "moiety" means a part or portion of an organic molecule that has a characteristic chemical property. As used herein, the term "reactive moiety" means a part or portion of an organic molecule that may react to form one or more bond(s) with an intermediate in a polymerization reaction, or with a polymer into which it has been incorporated. As used herein the term "intermediate in a polymerization reaction" means any combination of two or more monomer units that are capable of reacting to form one or more bond(s) to additional monomer unit(s) to continue a polymerization reaction or, alternatively, reacting with a reactive moiety of the reactive substituent on the photochromic material. For example, although not limiting herein, the reactive moiety may react with an intermediate in a polymerization reaction of a monomer or oligomer as a co-monomer in the polymerization reaction or may react as, for example and without limitation, a nucleophile or electrophile, that adds into the intermediate. Alternatively, the reactive moiety may react with a group (such as, but not limited to a hydroxyl group) on a polymer.

As used herein the term "residue of a reactive moiety" means that which remains after a reactive moiety has been reacted with a protecting group or an intermediate in a polymerization reaction. As used herein the term "protecting group" means a group that is removably bonded to a reactive moiety that prevents the reactive moiety from participating in a reaction until the group is removed. Optionally, the reactive substituents according to various non-limiting embodiments disclosed herein may further comprise a linking group. As used herein the term "linking group" means one or more group(s) or chain(s) of atoms that connect the reactive moiety to the photochromic material.

As used herein the term "compatiblizing substituent" means an arrangement of atoms that can facilitate integration of the photochromic material into another material or solvent. For example, according to various non-limiting embodiments disclosed herein, the compatiblizing substituent may facilitate integration of the photochromic material into a hydrophilic material by increasing the miscibility of the photochromic material in water or a hydrophilic polymeric, oligomeric, or monomeric material. According to other non-limiting embodiments, the compatiblizing substituent may facilitate integration of the photochromic material into a lipophilic material. Although not limiting herein, photochromic materials according to various non-limiting embodiments disclosed herein that comprise a compatiblizing substituent that facilitates integration into a hydrophilic material may be miscible in hydrophilic material at least to the extent of one gram per liter. Non-limiting examples of compatiblizing substitutents include those substitutents comprising the group -J, where -J represents the group —K or hydrogen, which are discussed herein below.

Further, it should be appreciated that some substituents may be both compatiblizing and reactive. For example, a substituent that comprises hydrophilic linking group(s) that connects a reactive moiety to the photochromic material may be both a reactive substituent and a compatiblizing substituent. As used herein, such substituents may be termed as either a reactive substituent or a compatiblizing substituent.

Further, according to any of the previously mentioned non-limiting embodiments, the indeno-fused naphthopyran may be free of spiro-cyclic groups at the 13-position of the indeno-fused naphthopyran. As used herein the phrase "free of spiro-cyclic groups at the 13-position" means that if the 13-position of the indeno-fused naphthopyran is di-substituted, the substituent groups do not together form a spiro-cyclic group.

Further, various non-limiting embodiments disclosed herein relate to photochromic materials comprising an indeno-fused naphthopyran and a group that extends the pi-conjugated system of the indeno-fused naphthopyran bonded at the 11-position thereof (as discussed above), wherein the indeno-fused naphthopyran is an indeno[2',3':3,4]naphtho[1,2-b]pyran, and wherein the 6-position and/or the 7-position of the indeno-fused naphthopyran may each independently be substituted with a nitrogen containing group or an oxygen containing group ($R^e$); and the 13-position of the indeno-fused naphthopyran may be di-substituted with $R^s$ and $R^c$. Other non-limiting embodiments disclosed herein relate to photochromic materials comprising an indeno-fused naphthopyran, wherein the 13-position of the indeno-fused naphthopyran is unsubstituted, mono-substituted or di-substituted, provided that if the 13-position of the indeno-fused naphthopyran is di-substituted, the substituent groups do not together form norbornyl, and wherein the photochromic material has an integrated extinction coefficient greater than $1.0 \times 10^6$ nm×mol$^{-1}$×cm$^{-1}$ as determined by integration of a plot of extinction coefficient of the photochromic material vs. wavelength over a range of wavelengths ranging from 320 nm to 420 nm, inclusive. Further, according to these non-limiting embodiments the integrated extinction coefficient may range from $1.1 \times 10^6$ to $4.0 \times 10^6$ nm×mol$^{-1}$×cm$^{-1}$ as determined by integration of a plot of extinction coefficient of the photochromic material vs. wavelength over a range of wavelengths ranging from 320 nm to 420 nm, inclusive. Still further, the photochromic materials according these non-limiting embodiments may comprise a group that extends the pi-conjugated system of the indeno-fused naphthopyran bonded at the 11-position thereof. Non-limiting examples of groups bonded at the 11-position of the indeno-fused naphthopyran that extend the pi-conjugated system of the indeno-fused naphthopyran include those discussed above.

One specific non-limiting embodiment disclosed herein provides a photochromic material comprising: (i) an indeno-fused naphthopyran chosen from an indeno[2',3':3,4]naphtho[1,2-b]pyran, an indeno[1',2':4,3]naphtho[2,1-b]pyran, and mixtures thereof, wherein the 13-position of the indeno-fused naphthopyran is unsubstituted, mono-substituted or di-substituted, provided that if the 13-position of the indeno-fused naphthopyran is di-substituted, the substituent groups do not together form norbornyl; and (ii) a group having at least one pendant halo-substituted group bonded thereto that extends the pi-conjugated system of the indeno-fused naphthopyran bonded at the 11-position thereof.

As previously discussed, any of the photochromic materials according to various non-limiting embodiments disclosed herein may comprise at least one of a reactive substituent and/or a compatiblizing substituent. Further, according to various non-limiting embodiments disclosed herein wherein the photochromic material comprises multiple reactive substituents and/or multiple compatiblizing substituents, each reactive substituent and each compatiblizing substituent may be independently chosen. Non-limiting examples of reactive and/or compatiblizing substituents that may be used in conjunction with the various non-limiting embodiments disclosed hereininclude those discussed above.

Non-limiting examples of groups that -A'- may represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- may represent according to various non-limiting embodiments include a diamine residue or a derivative thereof, wherein a first amino nitrogen of said diamine residue may form a bond with -A'-, the group that extends the pi-conjugated system of the indeno-fused naphthopyran bonded at the 11-position thereof, or a substituent or an available position on the indeno-fused naphthopyran, and a second amino nitrogen of said diamine residue may form a bond with -E-, -G- or -J; and an amino alcohol residue or a derivative thereof, wherein an amino nitrogen of said amino alcohol residue may form a bond with -A'-, the group that extends the pi-conjugated system of the indeno-fused naphthopyran bonded at the 11-position thereof, or a substituent or an available position on the indeno-fused naphthopyran, and an alcohol oxygen of said amino alcohol residue may form a bond with -E-, -G- or -J. Alternatively, according to various non-limiting embodiments disclosed herein the amino nitrogen of said amino alcohol residue may form a bond with -E-, -G- or -J, and said alcohol oxygen of said amino alcohol residue may form a bond with -A'-, the group that extends the pi-conjugated system of the indeno-fused naphthopyran bonded at the 11-position thereof, or a substituent or an available position on the indeno-fused naphthopyran.

Non-limiting examples of suitable diamine residues that -D- may represent include an aliphatic diamine residue; a cyclo aliphatic diamine residue, a diazacycloalkane residue, an azacyclo aliphatic amine residue, a diazacrown ether residue, and an aromatic diamine residue. Specific non-limiting examples diamine residues that may be used in conjunction with various non-limiting embodiments disclosed herein include the following:

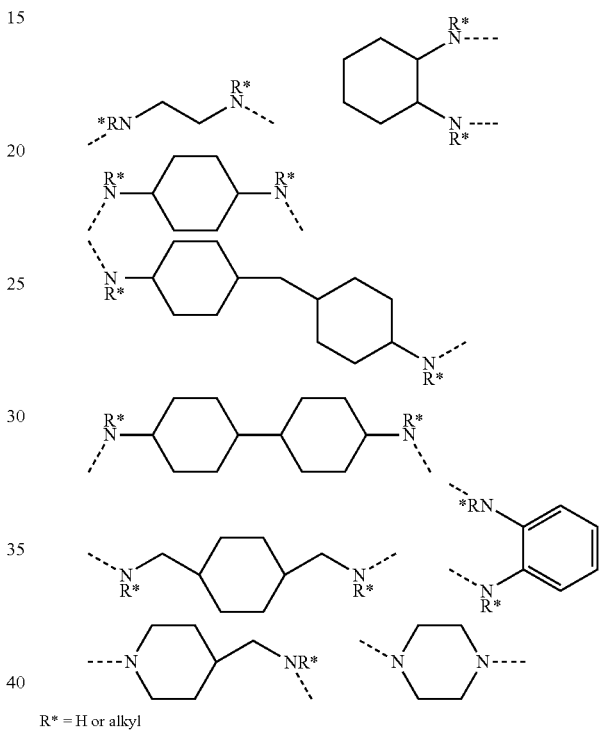

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that may be used in conjunction with various non-limiting embodiments disclosed herein include the following:

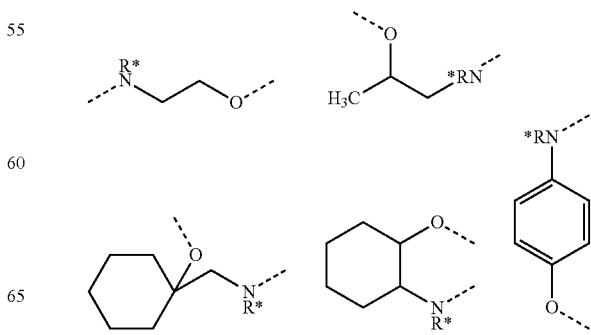

-continued

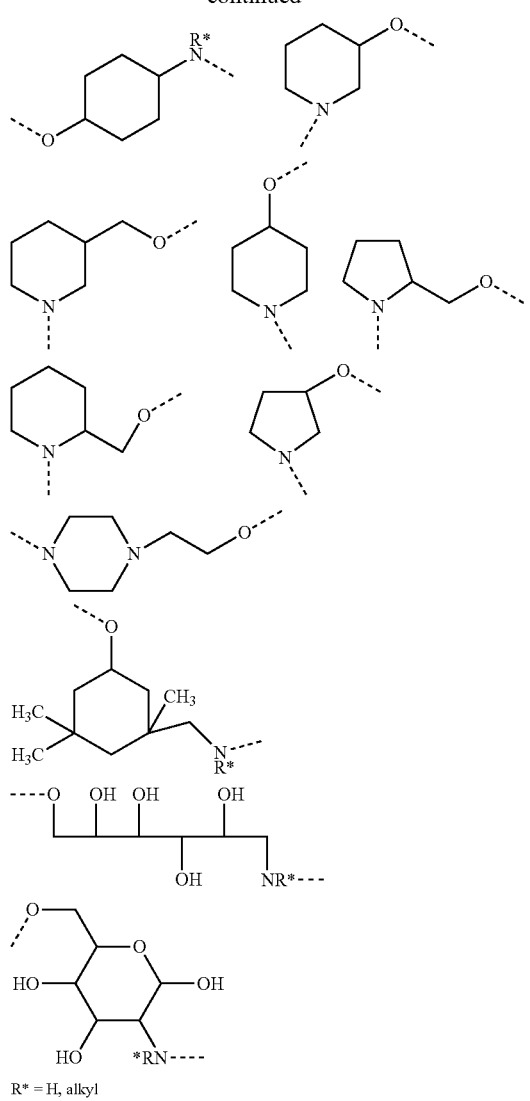

According to various non-limiting embodiments disclosed herein, -E- may represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- may represent include an aliphatic dicarboxylic acid residue, a cycloaliphatic dicarboxylic acid residue and an aromatic dicarboxylic acid residue. Specific non-limiting examples of dicarboxylic acid residues that may be used in conjunction with various non-limiting embodiments disclosed herein include the following:

-continued

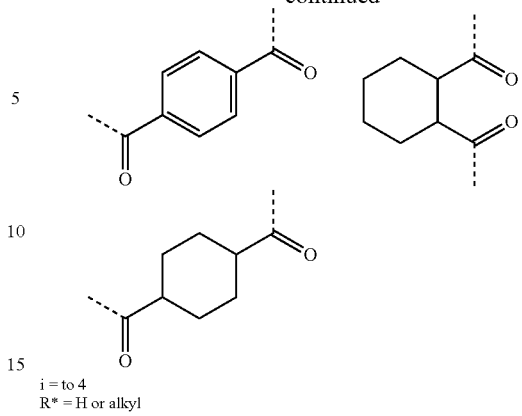

$i = 1$ to $4$
$R^* = H$ or alkyl

According to various non-limiting embodiments disclosed herein, -G- may represent a group $-[(OC_2H_4)_x(OC_3H_6)_y(OC_4H_8)_z]-O-$, wherein x, y and z are each independently chosen and range from 0 to 50, and a sum of x, y, and z ranges from 1 to 50; a polyol residue or a derivative thereof, wherein a first polyol oxygen of said polyol residue may form a bond with -A'-, -D-, -E-, the group that extends the pi-conjugated system of the indeno-fused naphthopyran bonded at the 11-position thereof, or a substituent or an available position on the indeno-fused naphthopyran, and a second polyol oxygen of said polyol may form a bond with -E- or -J; or a combination thereof, wherein the first polyol oxygen of the polyol residue forms a bond with a group $-[(OC_2H_4)_x(OC_3H_6)_y(OC_4H_8)_z]-$ (i.e., to form the group $-[(OC_2H_4)_x(OC_3H_6)_y(OC_4H_8)_z]-O-$), and the second polyol oxygen forms a bond with -E- or -J. Non-limiting examples of suitable polyol residues that -G- may represent include an aliphatic polyol residue, a cyclo aliphatic polyol residue and an aromatic polyol residue.

Specific non-limiting examples of polyols from which the polyol residues that -G- may represent may be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

According to various non-limiting embodiments disclosed herein, -J may represent a group —K, wherein —K represents a group such as, but not limited to, —CH$_2$COOH, —CH(CH$_3$)COOH, —C(O)(CH$_2$)$_w$COOH, —C$_6$H$_4$SO$_3$H, —C$_6$H$_{10}$SO$_3$H, —C$_4$H$_6$SO$_3$H, —C$_3$H$_6$SO$_3$H, —C$_2$H$_4$SO$_3$H and —SO$_3$H, wherein "w" ranges from 1 to 18. According to other non-limiting embodiments -J may represent hydrogen that forms a bond with an oxygen or a nitrogen of linking group to form a reactive moiety such as —OH or —NH. For example, according to various non-limiting embodiments disclosed herein, -J may represent hydrogen, provided that if -J represents hydrogen, -J is bonded to an oxygen of -D- or -G-, or a nitrogen of -D-.

According to still other non-limiting embodiments, -J may represent a group -L or residue thereof, wherein -L may represent a reactive moiety. For example, according to various non-limiting embodiments disclosed herein -L may represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

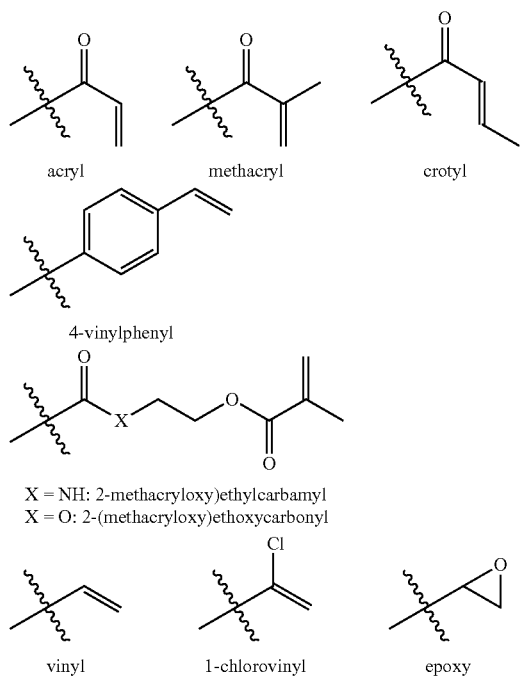

As previously discussed, -G- may represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol may be represented by q-(OH)$_a$ and the residue of the polyol may be represented by the formula —O-q-(OH)$_{a-1}$, wherein q is the backbone or main chain of the polyhydroxy compound and "a" is at least 2.

Further, as discussed above, one or more of the polyol oxygens of -G- may form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J may be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J may be produced by acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L chosen from acryl, methacryl, 2-(methacryloxy)ethylcarbamyl and epoxy, -L may be added by condensation of the polyol residue with acryloyl chloride, methacryloyl chloride, 2-isocyanatoethyl methacrylate or epichlorohydrin, respectively.

As discussed above, according to various non-limiting embodiments disclosed herein, a reactive substituent and/or a compatiblizing substituent may be bonded to group that extends the pi-conjugated system of the indeno-fused naphthopyran bonded at the 11-position of the indeno-fused naphthopyran. For example, as discussed above, the group that extends the pi-conjugated system of the indeno-fused naphthopyran bonded at the 11-position thereof may be an aryl or heteroaryl that is substituted with the reactive and/or compatiblizing substituent.

For example, the group that extends the pi-conjugated system may be a substituted aryl group (e.g., a phenyl group substituted with a trifluoromethyl) that is further substituted with a reactive substituent (e.g., a (2-methacryloxyethoxy) carbonyl which may be represented by -A'-G-J (as discussed above), wherein -A'- represents —C(=O)—, -G- represents —[OC$_2$H$_4$]O—, and -J represents methacryl.

Additionally or alternatively, a reactive and/or compatiblizing substituent may be bonded at a substituent or an available position on the indeno-fused naphthopyran ring other than at the 11-position. For example, although not limiting herein, in addition to or instead of having a reactive and/or compatiblizing substituent bonded to the group that extends the pi-conjugated system of the indeno-fused naphthopyran bonded at the 11-position of the indeno-fused naphthopyran, the 13-position of the indeno-fused naphthopyran may be mono- or di-substituted with a reactive and/or compatiblizing substituent. Further, if the 13-position is di-substituted, each substituent may be the same or different. In another non-limiting example, in addition to or instead of having a reactive and/or compatiblizing substituent bonded to the group that extends the pi-conjugated system of the indeno-fused naphthopyran bonded at the 11-position of the indeno-fused naphthopyran, a reactive and/or compatiblizing substituent may be substituted at the 3-position of an indeno[2',3':3,4]naphtho[1,2-b]pyran, the 2-position of an indeno[1',':4,3]naphtho[2,1-b]pyran, and/or the 6- or 7-positions of these indeno-fused naphthopyrans. Further, if the photochromic material comprises more than one reactive and/or compatiblizing substituent, each reactive and/or compatiblizing substituent may be the same as or different from one or more of the remaining reactive and/or compatiblizing substituents.

For example, according to one non-limiting embodiment, the group that extends the pi-conjugated system of the indeno-fused naphthopyran bonded at the 11-position thereof can be a substituted aryl group and the photochromic material further comprises a reactive substituent (e.g., a 3-(2-methacryloxyethyl)carbamyloxymethylenepiperidino-1-yl) group which may be represented by -D-J (as discussed above), wherein -D- represents an azacyclo aliphatic alcohol residue, wherein the nitrogen of the azacyclo aliphatic alcohol residue forms a bond with the indeno-fused naphthopyran at the 7-position, and the alcohol oxygen of the azacyclo aliphatic alcohol residue forms a bond with -J, wherein -J represents 2-(methacryloxy)ethylcarbamyl. Another non-limiting example of a photochromic material according to various non-limiting embodiments disclosed herein that has a reactive substituent at the 7-position thereof is a 3-(4-morpholinophenyl)-3-phenyl-6-methoxy-7-(3-(2-methacryloxyethyl)carbamyloxymethylenepiperidino-1-yl)-11-(4-trifluoromethyl)phenyl-13,13-dimethyl-3H,13H-indeno[2',3':3,4]naphtho[1,2-b]pyran.

One non-limiting example of a photochromic material according to various non-limiting embodiments disclosed herein that has a reactive substituent at the 3-position thereof is a 3-(4-(2-(2-methacryloxyethyl)carbamylethoxy)phenyl)-3-phenyl-6,7-dimethoxy-11-(2-trifluoromethyl)phenyl-13,13-dimethyl-3H,13H-indeno[2',3':3,4]naphtho[1,2-b]pyran.

Additional description of reactive substituents that may be used in connection with the photochromic materials described herein is set forth at col. 5, line 42 to col. 15, line 28, in U.S. Pat. No. 7,556,750, entitled PHOTOCHROMIC MATERIALS WITH REACTIVE SUBSTITUENTS, which is hereby specifically incorporated by reference herein. Still other non-limiting examples of reactive and/or compatiblizing substituents are set forth in U.S. Pat. No. 6,555,028, at col. 3, line 45 to col. 4, line 26, and U.S. Pat. No. 6,113,814 at col. 3, lines 30-64, which disclosures are hereby specifically incorporated by reference herein.

Methods of making photochromic materials that include the indeno-fused naphthopyrans according to the present invention are described here with reference to the general reaction schemes summarized and depicted in FIGS. 1 through 5 of the drawings. With reference to FIG. 1, there is depicted a reaction scheme for making substituted 7H-benzo[C]fluoren-5-ol compounds, that may be further reacted as shown in FIGS. 2 through 5 to form photochromic materials comprising an indeno-fused naphthopyran and a pendent halo-substituted group substituted pi-conjugation extending group bonded to the 11-position thereof, that extends the pi-conjugated system of the indeno-fused naphthopyran. The reaction schemes depicted in FIGS. 1-5 are presented for purposes of illustration, and as such are not intended to be limiting with regard to the scope of the present invention.

With reference to FIG. 1, a solution of a γ-substituted benzoyl chloride, represented by structure (a) in FIG. 1, and benzene, represented by structure (b) in FIG. 1, which may have one or more substituents $\gamma^1$, in methylene chloride are added to a reaction flask. Suitable γ-substituents include, for example and without limitation, halogen. Suitable $\gamma^1$ substituents include, for example and without limitation, those groups as described previously herein with regard to $R^e$, depending on what position a particular $\gamma^1$ substituent is bonded to. Anhydrous aluminum chloride catalyzes the Friedel-Crafts acylation to give a substituted benzophenone represented by structure (c) in FIG. 1. This material is then reacted in a Stobbe reaction with dimethyl succinate to produce a mixture of half-esters, one of which is represented by structure (d) in FIG. 1. Thereafter the half-esters are reacted in acetic anhydride and toluene at an elevated temperature to produce, after recrystallization, a mixture of substituted naphthalene compounds, one of which is represented by structure (e) in FIG. 1. The mixture of substituted naphthalene compounds is then reacted with methyl magnesium chloride to produce a mixture of substituted naphthalene compounds, one of which is represented by structure (f) in FIG. 1. The mixture of substituted naphthalene compounds is then cyclized with dodecylbenzene sulfonic acid to afford a mixture of 7H-benzo[C]fluoren-5-ol compounds, one of which is represented by structure (g) in FIG. 1.

Figure 2:
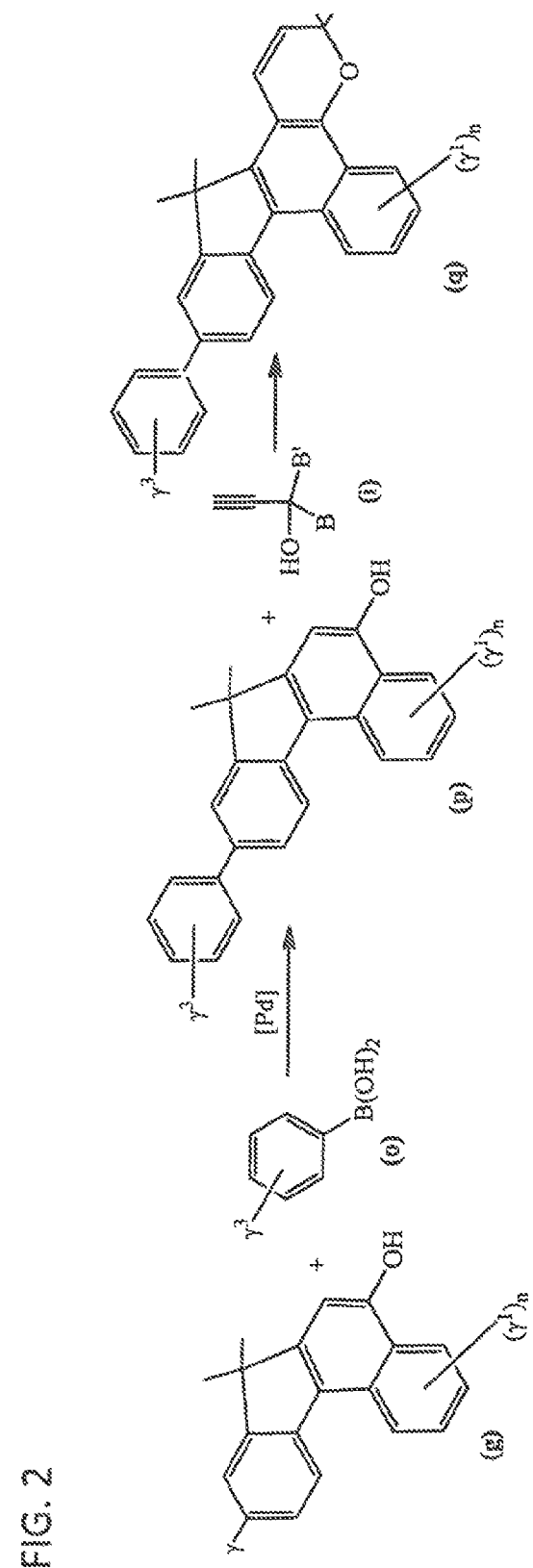
FIGS. 2 through 5 are representative schematic diagrams of reaction schemes that may be used in making photochromic materials according to the present invention.

With reference to FIG. 2, the 7H-benzo[C]fluoren-5-ol compound represented by structure (g) may be reacted with a phenyl boronic acid represented by structure (O), which may be substituted with a pendent halo-substituted group represented by $\gamma^3$ as shown in FIG. 2, to form the 9-(4-$\gamma^3$-phenyl)-7H-benzo[C]fluoren-5-ol compound represented by structure (p) in FIG. 2. Examples of suitable boronic acids include, without limitation, 4-(trifluoromethyl)phenylboronic acid, and 4-(perfluoroethyl)phenylboronic acid. The compound represented by structure (p) may be further reacted with a propargyl alcohol represented by structure (i) to produce the indeno-fused naphthopyran (represented by structure (q) in FIG. 2), wherein a pendent halo-substituted group substituted phenyl group that extends the pi-conjugated system of the indeno-fused naphthopyran is bonded at the 11-position thereof. Although not required, according to various non-limiting embodiments disclosed herein and as shown in FIG. 2, the phenyl group bonded at the 11-position may be further substituted, in addition to the one or more pendent halo-substituted groups (as described previously herein, for example, with regard to $R^a$). Further, the substituted phenyl at the 11-position may, in addition to the pendent halo-substituted group, have up to four substituents, and those substituents may be a variety of different substituents at any of the positions ortho, meta or para to the indeno-fused naphthopyran.

Figure 3:
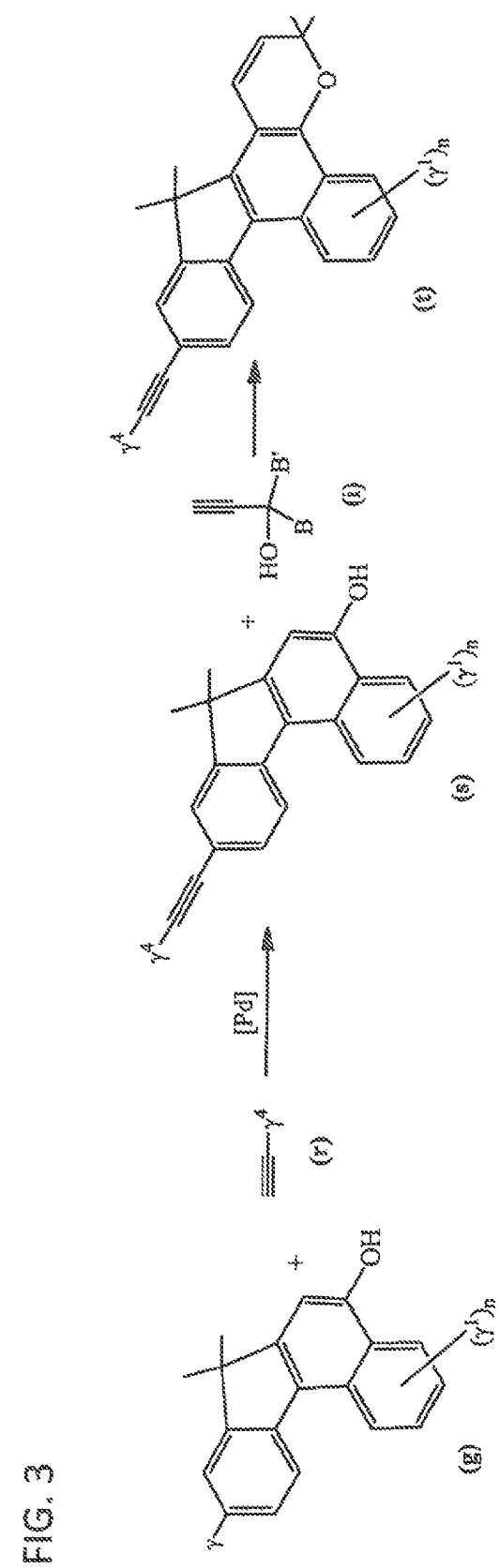

With reference to FIG. 3, the 7H-benzo[C]fluoren-5-ol compound represented by structure (g) may be coupled in the presence of a palladium catalysis with a terminal alkyne group represented by structure (r), which may be substituted with a pendent halo-substituted group represented by $\gamma^4$ as shown in FIG. 3, to form the 9-alkynyl-7H-benzo[C]fluoren-5-ol compound represented by structure '(s)' in FIG. 3. Suitable terminal alkynes include, for example, trifiouromethyl-acetylene and perfluoroethyl-acetylene. The compound represented by structure '(s)' may be further reacted with a propargyl alcohol represented by structure (i) to produce the indeno-fused naphthopyran (represented by structure (t) in FIG. 3) having a pendent halo-substituted group substituted alkynyl group that extends the pi-conjugated system of the indeno-fused naphthopyran bonded at the 11-position thereof.

Figure 4:
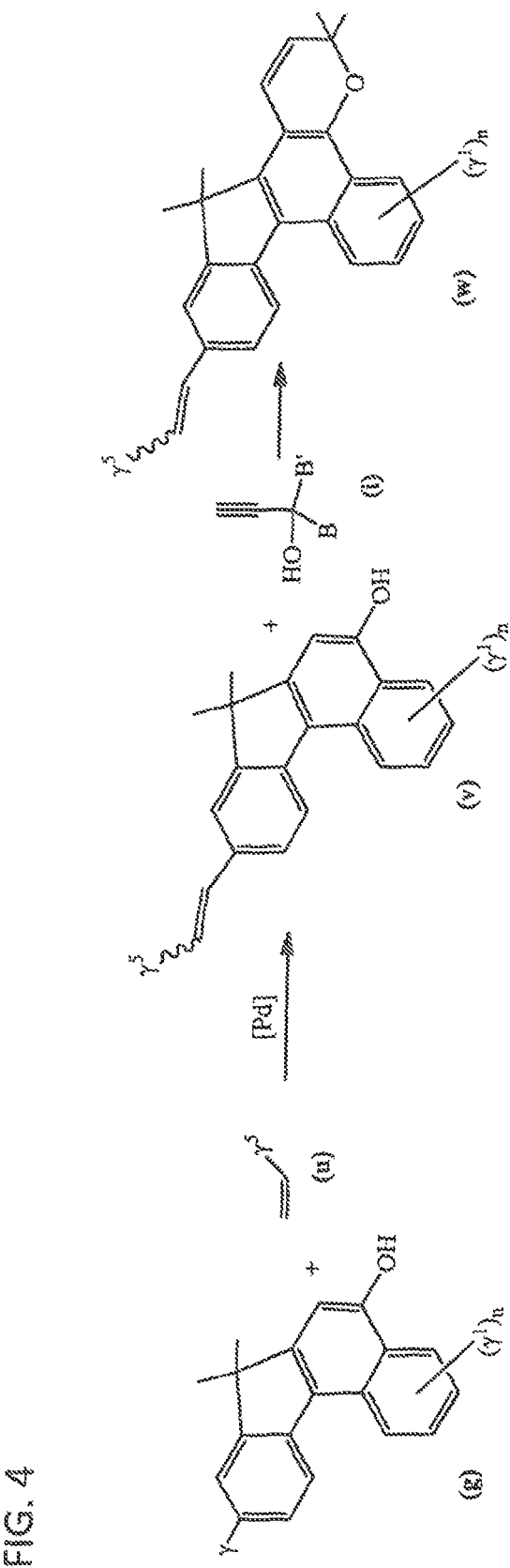

With reference to FIG. 4, the 7H-benzo[C]fluoren-5-ol compound represented by structure (g) may be reacted with an alkene represented by structure (u), which may be substituted with a pendent halo-substituted group represented by $\gamma^5$ as shown in FIG. 4, to form the 9-alkenyl-7H-benzo[C]fluoren-5-ol compound represented by structure (v) in FIG. 4. Examples of suitable alkenes include, without limitation trifluoromethyl-ethene and perfluoroethyl-ethene. The compound represented by structure (v) may be further reacted with a propargyl alcohol represented by structure (i) to produce the indeno-fused naphthopyran (represented by structure (w) in FIG. 4) having a pendent halo-substituted group substituted alkenyl group that extends the pi-conjugated system of the indeno-fused naphthopyran bonded at the 11-position thereof.

Figure 5:
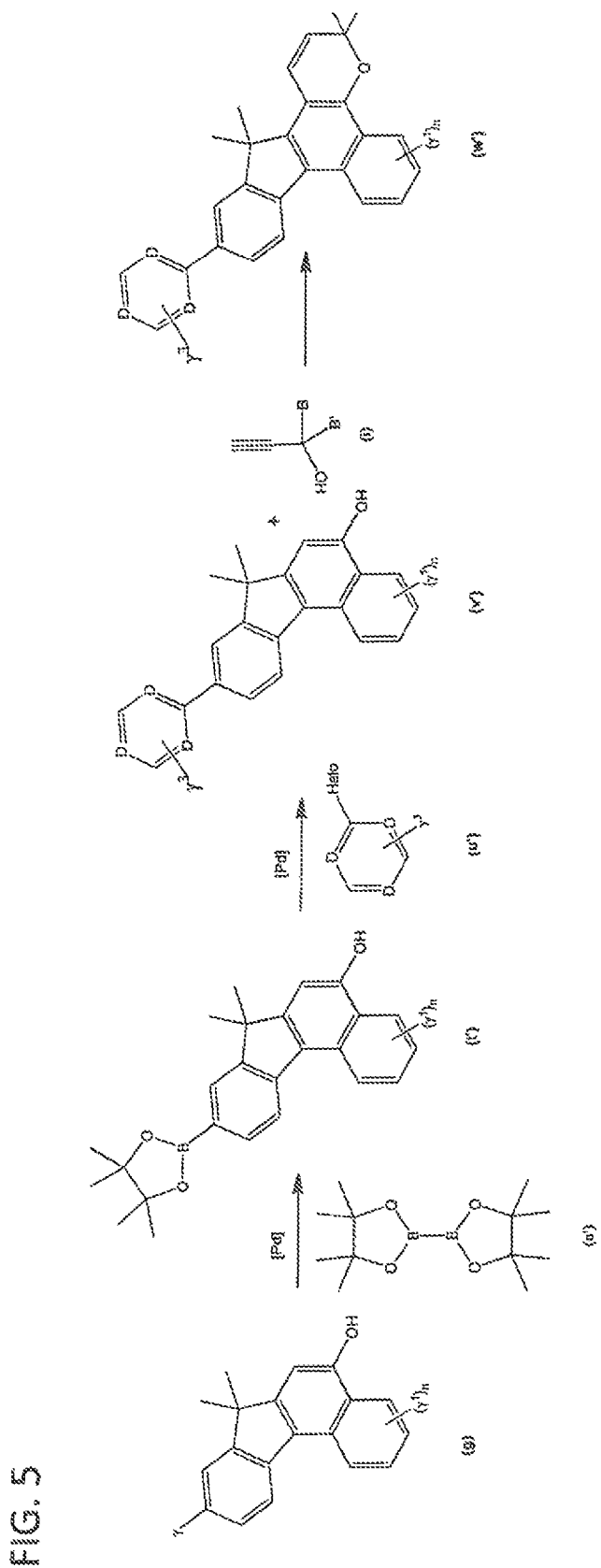

With reference to FIG. 5, the 7H-benzo[C]fluoren-5-ol compound represented by structure (g) is reacted with 4,4,4', 4',5,5,5',5'-octamethyl-2,2'-bi(1,3,2-dioxaborolane) represented by structure (o') in the presence of a palladium catalyst to form the compound represented by structure (t'). The latter can be reacted with a halogenated heteroaryl represented by structure (u') in which D is nitrogen or carbon provided that at least one D is nitrogen and the halo group is chosen from Br, Cl or I, and which is substituted with a pendent halo-substituted group represented by $\gamma^3$ to form the compound represented by structure (v'). An example of a suitable halogenated heteroaryl group represented by structure (u') is 3-(trifluoromethyl)-2-bromopyridine. The compound represented by structure (v') may be further reacted with a propargyl alcohol represented by structure (i) to produce the indeno-fused naphthopyran represented by structure (w').

Figure 6:
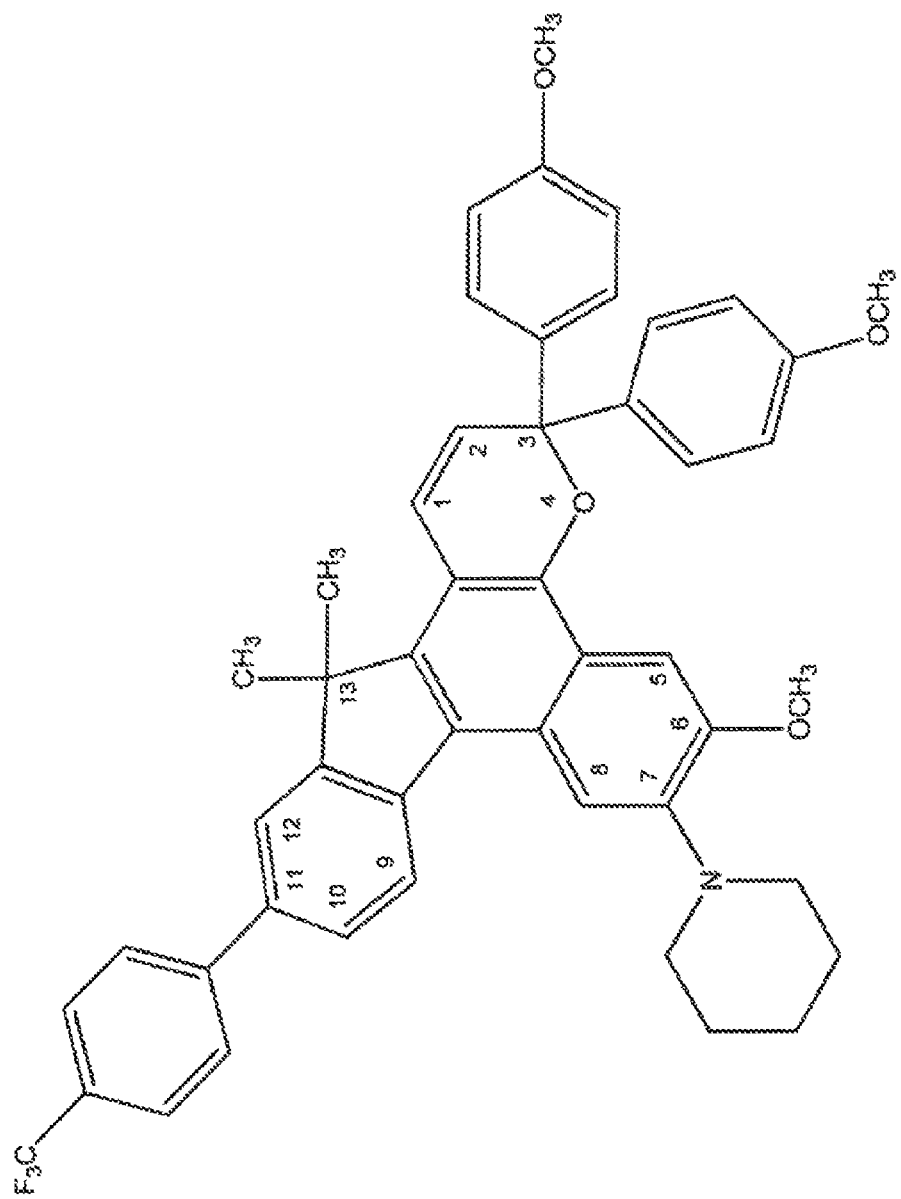
FIG. 6 is a representative general chemical formula of an indeno-fused naphthopyran according to the present invention.
Figure 7:
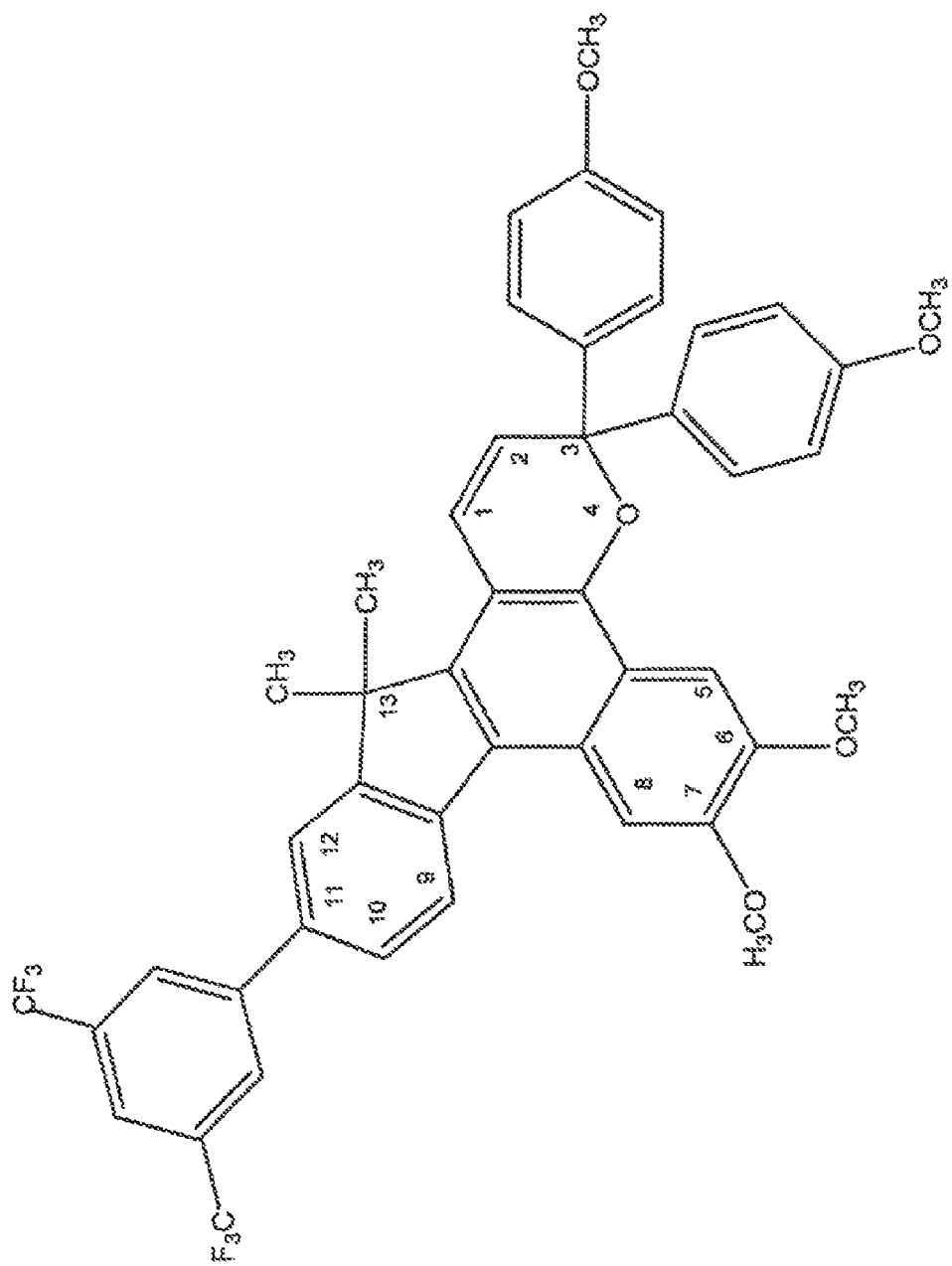
FIG. 7 is a representative general chemical formula of an indeno-fused naphthopyran according to the present invention.
Figure 8:
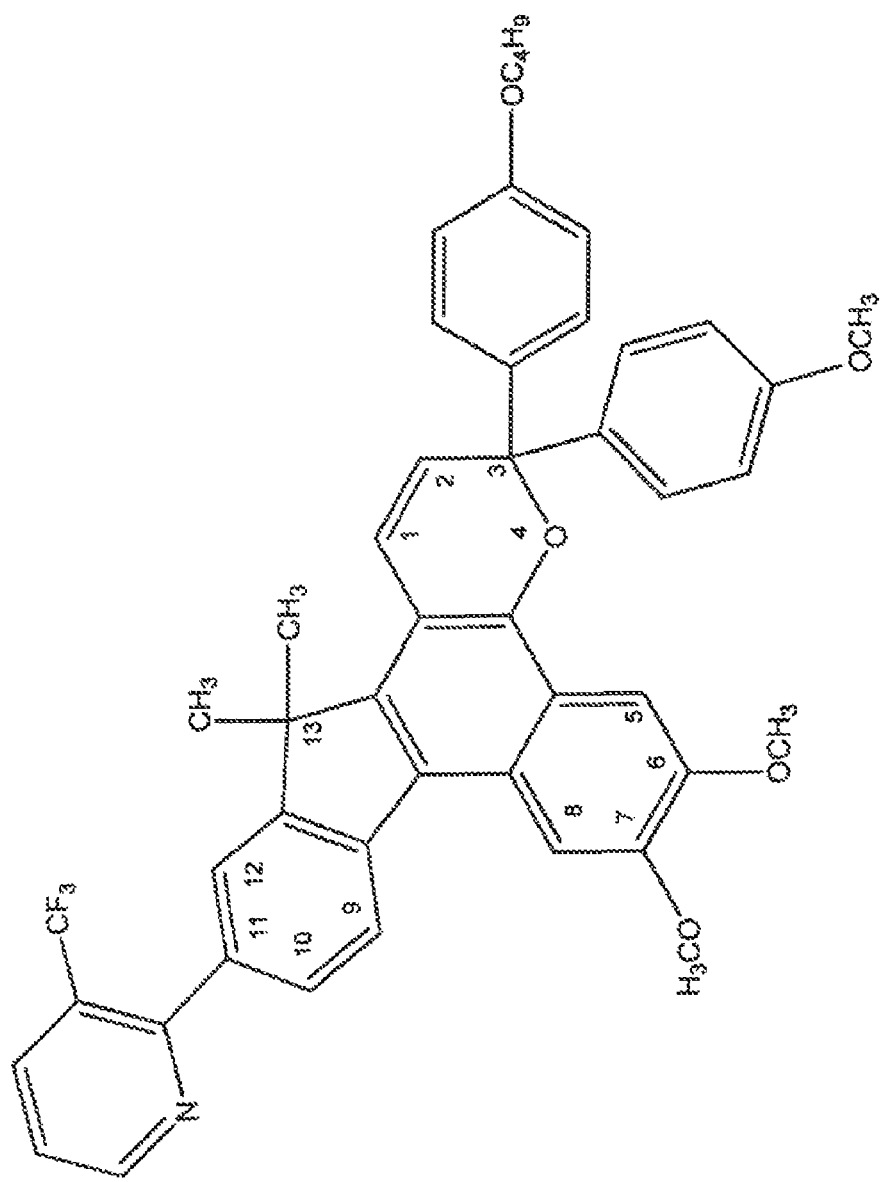
FIG. 8 is a representative general chemical formula of an indeno-fused naphthopyran according to the present invention.

With reference to FIGS. 6-8, each graphic formula represents a compound of the present invention. FIG. 6 represents 3,3-di-(4-methoxyphenyl-6-methoxy-7-piperidino-11-(4-trifluoromethyl)phenyl-13,13-dimethyl-3H,13H-indeno[2', 3':3,4]naphtho[1,2-b]pyran included herein as Example 4. FIG. 7 represents 3,3-di(4-methoxyphenyl)-6,7-dimethoxy-11-(3,5-bis(trifluoromethyl)phenyl)-13,13-dimethyl-3H, 13H-indeno[2',3':3,4]naphtho[1,2-b]pyran included herein as Example 2. FIG. 8 represents 3-(4-butoxyphenyl)-3-(4-methoxyphenyl)-6,7-dimethoxy-11-(3-(trifluoromethyl)pyridin-2-yl)-13,13-dimethyl-3H,13H-indeno[2',3':3,4]naphtho[1,2-b]pyran included herein as Example 13.

Further, non-limiting examples of methods of forming benzofurano-fused naphthopyrans, indolo-fused naphthopyrans, and/or benzothieno-fused naphthopyrans that may be useful (with appropriate modifications that will be recognized by those skilled) in forming the benzofurano-fused naphthopyrans, indolo-fused naphthopyrans and/or benzothieno-fused naphthopyrans according to various non-limiting embodiments disclosed herein are set forth in U.S. Pat. No. 5,651,923 at col. 6, line 43 to col. 13, line 48, which disclosure is hereby specifically incorporated by reference herein; U.S. Pat. No. 6,018,059 at column 6, line 1 to column 7, line 64, which disclosure is hereby specifically incorporated by reference herein; and U.S. Pat. No. 6,392,043 at column 6, line 5 to column 10, line 10, which disclosure is hereby specifically incorporated by reference herein.

In an embodiment of the present invention, the photochromic material of the present invention, including the indeno-fused naphthopyrans as described, for example, with reference to FIGS.-(1) and/or -(2), displays hyperchromic absorption of electromagnetic radiation having a wavelength from 320 nm to 420 nm, as compared to a comparative photochromic material comprising a comparable indeno-fused naphthopyran that is substantially free of the pi-conjugation extending group bonded to the 11-position of the comparable indeno-fused naphthopyran. As used herein and in the claims, the term "hyperchromic absorption" refers to an increase in the absorption of electromagnetic radiation by a photochromic material having a pi-conjugation extending group (e.g., as described with reference to $R^a$) bonded to the 11-position of the indeno-fused naphthopyran, on a per molecule basis as compared to a comparable photochromic material that does not have a pi-conjugation extending group bonded to the 11-position of the comparable indeno-fused naphthopyran.

The present invention also relates to an optical element that includes one or more indeno-fused naphthopyrans according to the present invention. In particular, the optical element that includes one or more indeno-fused naphthopyrans that includes: a pi-conjugation extending group bonded to the 11-position of the indeno-fused, the pi-conjugation extending group having at least one pendent halo-substituted group bonded thereto, the pi-conjugation extending group extending the pi-conjugation system of the indeno-fused naphthopyran; an ether group bonded to the 6 or 7-position of the indeno-fused naphthopyran, the ether-oxygen of the ether group being bonded to the 6 or 7-position; and/or an amino group bonded to the 6 or 7-position of the indeno-fused naphthopyran, the amine-nitrogen of said amino group being bonded to the 6 or 7-position, the amino group being selected from secondary amines or tertiary amines. The 13-position of the indeno-fused naphthopyran, incorporated into the optical element, is substantially free of spiro-substituents. Optical elements that may include the photochromic materials, including the indeno-fused naphthopyrans, of the present invention are described in further detail herein below. As discussed above, the photochromic materials according to various non-limiting embodiments disclosed herein may be incorporated into at least a portion of an organic material, such as a polymeric, oligomeric or monomeric material to form a photochromic composition, which may be used, for example and without limitation, to form photochromic articles, such as optical elements, and coating compositions that may be applied to various substrates. As used herein the terms "polymer" and "polymeric material" refer to homopolymers and copolymers (e.g., random copolymers, block copolymers, and alternating copolymers), as well as blends and other combinations thereof. As used herein the terms "oligomer" and "oligomeric material" refer to a combination of two or more monomer units that is capable of reacting with additional monomer unit(s). As used herein the term "incorporated into" means physically and/or chemically combined with. For example, the photochromic materials according to various non-limiting embodiments disclosed herein may be physically combined with at least a portion of an organic material, for example and without limitation, by mixing or imbibing the photochromic material into the organic material; and/or chemically combined with at least a portion of an organic material, for example and without limitation, by copolymerization or otherwise bonding the photochromic material to the organic material.

Further, it is contemplated that the photochromic materials according to various non-limiting embodiments disclosed herein may each be used alone, in combination with other photochromic materials according to various non-limiting embodiments disclosed herein, or in combination with an appropriate complementary conventional photochromic material. For example, the photochromic materials according to various non-limiting embodiments disclosed herein may be used in conjunction with conventional photochromic materials having activated absorption maxima within the range of 300 to 1000 nanometers. Further, the photochromic materials according to various non-limiting embodiments disclosed herein may be used in conjunction with a complementary conventional polymerizable or a compatiblized photochromic material, such as for example, those disclosed in U.S. Pat. Nos. 6,113,814 (at col. 2, line 39 to col. 8, line 41), and 6,555,028 (at col. 2, line 65 to col. 12, line 56), which disclosures are hereby specifically incorporated by reference herein.

As discussed above, according to various non-limiting embodiments disclosed herein, the photochromic compositions may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Various non-limiting embodiments disclosed herein provide a photochromic composition comprising an organic material, said organic material being at least one of polymeric material, an oligomeric material and a monomeric material, and a photochromic material according to any of the non-limiting embodiments of set forth above incorporated into at least a portion of the organic material. According to various non-limiting embodiments disclosed herein, the photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof. For example, although not limiting herein, the photochromic material may be linked to the organic material through a reactive substituent.

According to one non-limiting embodiment wherein the organic material is a polymeric material, the photochromic material may be incorporated into at least a portion of the polymeric material or at least a portion of the monomeric material or oligomeric material from which the polymeric material is formed. For example, photochromic materials according to various non-limiting embodiments disclosed herein that have a reactive substituent may be bonded to an organic material such as a monomer, oligomer, or polymer having a group with which a reactive moiety may be reacted, or the reactive moiety may be reacted as a co-monomer in the polymerization reaction from which the organic material is formed, for example, in a co-polymerization process.

As discussed above, the photochromic compositions according to various non-limiting embodiments disclosed herein may comprise an organic material chosen from a polymeric material, an oligomeric material and/or a monomeric material. Examples of polymeric materials that may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly (vinyl alcohol); poly(vinyl chloride); poly(vinylidene chloride); polyurethanes; polythiourethanes; thermoplastic polycarbonates; polyesters; poly(ethylene terephthalate); polystyrene; poly(□-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments wherein transparency of the photochromic composition is desired, the organic material may be a transparent. polymeric material. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material may be an optical resins sold by PPG Industries, Inc. under the CR-designation, e.g., CR-307, CR-407, and CR-607.

According to one specific non-limiting embodiment, the organic material may be a polymeric material which is chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

As previously discussed, it has been observed by the inventors that the photochromic materials according to certain non-limiting embodiments disclosed herein may display hyperchromic absorption of electromagnetic radiation having a wavelength from 320 nm to 420 nm as compared to a photochromic materials comprising a comparable indeno-fused naphthopyran without the group that extends the pi-conjugated system (having at least one pendant halo-substituted group bonded thereto) of the comparable indeno-fused naphthopyran bonded at the 11-position thereof. Accordingly, photochromic compositions comprising the photochromic materials according to various non-limiting embodiments disclosed herein may also displays increased absorption of electromagnetic radiation having a wavelength from 320 nm to 420 nm as compared to a photochromic composition comprising a comparable indeno-fused naphthopyran without the group that extends the pi-conjugated system of the comparable indeno-fused naphthopyran bonded at the 11-position thereof.

Additionally, as previously discussed, since the photochromic materials according to certain non-limiting embodiments disclosed herein may display hyperchromic properties as discussed above, it is contemplated that the amount or concentration of the photochromic material present in photochromic compositions according to various non-limiting embodiments disclosed herein may be reduced as compared to the amount or concentration of a conventional photochromic materials that is typically required to achieve a desired optical effect. Since it may be possible to use less of the photochromic materials according to certain non-limiting embodiments disclosed herein than conventional photochromic materials while still achieving the desired optical effects, it is contemplated that the photochromic materials according to various non-limiting embodiments disclosed herein may be advantageously employed in applications wherein it is necessary or desirable to limit the amount of photochromic material used.

Further, as previously discussed, it has been observed by the inventors that the photochromic materials according to certain non-limiting embodiments disclosed herein the may have a closed-form absorption spectrum for electromagnetic radiation having a wavelength ranging from 320 nm to 420 nm that is bathochromically shifted as compared to a closed-form absorption spectrum for electromagnetic radiation having a wavelength ranging from 320 nm to 420 nm of a photochromic material comprising a comparable indeno-fused naphthopyran without the group having a pendant halo-substituted group that extends the pi-conjugated system of comparable the indeno-fused naphthopyran bonded at the 11-position thereof. Accordingly, photochromic compositions comprise the photochromic materials according to various non-limiting embodiments disclosed herein may also have an absorption spectrum for electromagnetic radiation having a wavelength ranging from 320 nm to 420 nm that is bathochromically shifted as compared to an absorption spectrum for electromagnetic radiation having a wavelength ranging from 320 nm to 420 nm of a photochromic composition comprising a comparable indeno-fused naphthopyran without the group having a pendant halo-substituted group that extends the pi-conjugated system of the comparable indeno-fused naphthopyran bonded at the 11-position thereof.

As previously discussed, the present invention further contemplates photochromic articles, such as optical elements, made using the photochromic materials and compositions according to various non-limiting embodiments disclosed herein. As used herein the term "optical" means pertaining to or associated with light and/or vision. The optical elements according to various non-limiting embodiments disclosed herein may include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation therethrough. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Various non-limiting embodiments disclosed herein provide photochromic articles, such as optical elements, comprising a substrate and a photochromic material according to any of the non-limiting embodiments discussed above connected to a portion of the substrate. As used herein, the term "connected to" means associated with, either directly or indirectly through another material or structure.

According to various non-limiting embodiments disclosed herein wherein the substrate of the photochromic article comprises a polymeric material, the photochromic material may be connected to at least a portion of the substrate by incorporating the photochromic material into at least a portion of the polymeric material of the substrate, or by incorporating the photochromic material into at least a portion of the oligomeric or monomeric material from which the substrate is formed. For example, according to one non-limiting embodiment, the photochromic material may be incorporated into the polymeric material of the substrate by the cast-in-place method or by imbibition. Imbibition and the cast-in-place method are discussed below.

According to still other non-limiting embodiments, the photochromic material may be connected to at least a portion of the substrate of the photochromic article as part of at least partial coating that is connected to at least a portion of a substrate. According to this non-limiting embodiment, the substrate may be a polymeric substrate or an inorganic substrate (such as, but not limited to, a glass substrate). Further, the photochromic material may be incorporated into at least a portion of a coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

The at least partial coating comprising the photochromic material may be connected to at least a portion of the substrate, for example, by applying a coating composition comprising the photochromic material to at least a portion of a surface of the substrate, and at least partially setting the coating composition. Additionally or alternatively, the at least partial coating comprising the photochromic material may be connected to the substrate, for example, through one or more additional at least partial coatings. For example, while not limiting herein, according to various non-limiting embodiments, an additional coating composition may be applied to a portion of the surface of the substrate, at least partially set, and thereafter the coating composition comprising the photochromic material may be applied over the additional coating and at least partially set. Non-limiting methods of applying coatings compositions to substrates are discussed herein below.

Non-limiting examples of additional coatings and films that may be used in conjunction with the photochromic articles disclosed herein include primer coatings and films; protective coatings and films, including transitional coatings and films and abrasion resistant coatings and films; antireflective coatings and films; conventional photochromic coating and films; and polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

Non-limiting examples of primer coatings and films that may be used in conjunction with various non-limiting embodiments disclosed herein include coatings and films comprising coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating and film" means a coating or film that aids in creating a gradient in properties between two coatings or films, or a coating and a film. For example, although not limiting herein, a transitional coating may aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which may be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

As discussed above, according to various non-limiting embodiments, an additional at least partial coating or film may be formed on the substrate prior to forming the coating comprising the photochromic material according to various non-limiting embodiments disclosed herein on the substrate. For example, according to certain non-limiting embodiments a primer coating may be formed on the substrate prior to applying the coating composition comprising the photochromic material. Additionally or alternatively, the additional at least partial coating or film may be formed on the substrate after forming coating comprising the photochromic material according to various non-limiting embodiments disclosed herein on the substrate, for example, as an overcoating. For example, according to certain non-limiting embodiments, a transitional coating may be formed over the coating comprising the photochromic material, and an abrasion resistant coating may be formed over the transitional coating.

Another non-limiting embodiment provides an optical element adapted for use behind a substrate that blocks a substantial portion of electromagnetic radiation in the range of 320 nm to 390 nm, the optical element comprising a photochromic material comprising an indeno-fused naphthopyran and a group that extends the pi-conjugated system of the indeno-fused naphthopyran bonded at the 11-position thereof connected to at least a portion of the optical element, wherein the at least a portion of the optical element absorbs a sufficient amount of electromagnetic radiation having a wavelength greater than 390 nm passing through the substrate that blocks a substantial portion of electromagnetic radiation in the range of 320 nm to 390 nm such that the at least a portion of the optical element transforms from a first state to a second state. For example, according to this non-limiting embodiment, the first state may be a bleached state and the second state may be a colored state that corresponds to the colored state of the photochromic material(s) incorporated therein.

As previously discussed, many conventional photochromic materials require electromagnetic radiation having a wavelength ranging from 320 nm to 390 nm to cause the photochromic material to transformation from a closed-form to an open-form (e.g., from a bleached state to a colored state). Therefore, conventional photochromic materials may not achieve their fully-colored state when use in applications that are shielded from a substantial amount of electromagnetic radiation in the range of 320 nm to 390 nm. Further, as previous discussed, it has been observed by the inventors that photochromic material according to certain non-limiting embodiments disclosed herein may display both hyperchromic and bathochromic properties. That is, the indeno-fused naphthopyrans comprising a group that extends the pi-conjugated system of the indeno-fused naphthopyran at the 11-position thereof according to certain non-limiting embodiments disclosed herein may not only display hyperchromic absorption of electromagnetic radiation as discussed above, but may also have a closed-form absorption spectrum for electromagnetic radiation having a wavelength ranging from 320 nm to 420 nm that is bathochromically shifted as compared to a closed-form absorption spectrum for electromagnetic radiation having a wavelength ranging from 320 nm to 420 nm of a comparable indeno-fused naphthopyran without the group that extends the pi-conjugated system of the comparable indeno-fused naphthopyran bonded at the 11-position thereof. Accordingly, the photochromic materials according to certain non-limiting embodiments disclosed herein may absorb a sufficient amount of electromagnetic radiation passing through a substrate that blocks a substantial portion of electromagnetic radiation having a wavelength ranging from 320 to 390 nm such that the photochromic material may transform from a closed-form to an open-form. That is, the amount of electromagnetic radiation having a wavelength of greater than 390 nm that is absorbed by the photochromic materials according to various non-limiting embodiments disclosed herein may be sufficient to permit the photochromic materials to transform from a closed-form to an open-form, thereby enabling their use behind a substrate that blocks a substantial portion of electromagnetic radiation having a wavelength ranging from 320 nm to 390 nm.

Non-limiting methods of making photochromic compositions and photochromic articles, such as optical elements, according to various non-limiting embodiments disclosed herein will now be discussed. One non-limiting embodiment provides a method of making a photochromic composition, the method comprising incorporating a photochromic material into at least a portion of an organic material. Non-limiting methods of incorporating photochromic materials into an organic material include, for example, mixing the photochromic material into a solution or melt of a polymeric, oligomeric, or monomeric material, and subsequently at least partially setting the polymeric, oligomeric, or monomeric material (with or without bonding the photochromic material to the organic material); and imbibing the photochromic material into the organic material (with or without bonding the photochromic material to the organic material).

Another non-limiting embodiment provides a method of making a photochromic article comprising connecting a photochromic material according to various non-limiting embodiments discussed above, to at least a portion a substrate. For example, if the substrate comprises a polymeric material, the photochromic material may be connected to at least a portion of the substrate by at least one of the cast-in-place method and by imbibition. For example, in the cast-in-place method, the photochromic material may be mixed with a polymeric solution or melt, or other oligomeric and/or monomeric solution or mixture, which is subsequently cast into a mold having a desired shape and at least partially set to form the substrate. Optionally, according to this non-limiting embodiment, the photochromic material may be bonded to a portion of the polymeric material of the substrate, for example, by co-polymerization with a monomeric precursor thereof. In the imbibition method, the photochromic material may be diffuse into the polymeric material of the substrate after it is formed, for example, by immersing a substrate in a solution containing the photochromic material, with or without heating. Thereafter, although not required, the photochromic material may be bonded with the polymeric material.

Other non-limiting embodiments disclosed herein provide a method of making an optical element comprising connecting a photochromic material to at least a portion of a substrate by at least one of in-mold casting, coating and lamination. For example, according to one non-limiting embodiment, wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomeric or monomeric solution or mixture is cast over the coating and at least partially set. After setting, the coated substrate is removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

According to still another non-limiting embodiment, wherein the substrate comprises a polymeric material or an inorganic material such as glass, the photochromic material may be connected to at least a portion of a substrate by coating. Non-limiting examples of suitable coating methods include spin coating, spray coating (e.g., using a liquid or powder coating), curtain coating, roll coating, spin and spray coating, over-molding, and combinations thereof. For example, according to one non-limiting embodiment, the photochromic material may be connected to the substrate by over-molding. According to this non-limiting embodiment, a coating composition comprising the photochromic material (which may be a liquid coating composition or a powder coating composition as previously discussed) may be applied to a mold and then the substrate may be placed into the mold such that the substrate contacts the coating causing it to spread over at least a portion of the surface of the substrate. Thereafter, the coating composition may be at least partially set and the coated substrate may be removed from the mold. Alternatively, over-molding may be done by placing the substrate into a mold such that an open region is defined between the substrate and the mold, and thereafter injecting a coating composition comprising the photochromic material into the open region. Thereafter, the coating composition may be at least partially set and the coated substrate may be removed from the mold.

Additionally or alternatively, a coating composition (with or without a photochromic material) may be applied to a substrate (for example, by any of the foregoing methods), the coating composition may be at least partially set, and thereafter, a photochromic material may be imbibed (as previously discussed) into the coating composition.

According to yet another non-limiting embodiment, wherein the substrate comprises a polymeric material or an inorganic material such as glass, the photochromic material may be connected to at least a portion of a substrate by lamination. According to this non-limiting embodiment, a film comprising the photochromic material may be adhered or otherwise connect to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, various non-limiting embodiments disclosed herein contemplate the use of various combinations of the foregoing methods to form photochromic articles according to various non-limiting embodiments disclosed herein. For example, and without limitation herein, according to one non-limiting embodiment, a photochromic material may be connected to substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating and/or lamination methods discussed above.

Further, it will be appreciated by those skilled in the art that the photochromic compositions and articles according to various non-limiting embodiments disclosed herein may further comprise other additives that aid in the processing and/or performance of the composition or article. Non-limiting examples of such additives include from photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

According to various non-limiting embodiments, the photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein is not critical provided that a sufficient amount is used to produce the desired effect. It should be appreciated that the particular amount of the photochromic material used may depend on a variety of factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent based on the weight of the organic material.

Various non-limiting embodiments disclosed herein will now be illustrated in the following non-limiting examples.

EXAMPLES

In Part 1 of the Examples, the synthesis procedures used to make photochromic materials according to various non-limiting embodiments disclosed herein are set forth in Examples 1-13, and the procedures used to make the comparative photochromic materials are described in Comparative Examples (CE) 1-10. In Part 2, the photochromic performance testing is described. In Part 3, the test results are reported.

Part 1

Photochromic Materials—Synthesis

Example 1

Step 1

Into a 3 liter reaction (3 neck) flask was added 2,3-dimethoxy-7,7-dimethyl-9-bromo-7H-benzo[C]fluoren-5-ol (170 grams) the product of Step 5 of Example 1 in U.S. Patent Publication 2006-0228557, which disclosure is incorporated herein by reference, 4-trifluoromethyl phenyl boronic acid (100 g), $Na_2CC_3$ (93 g), 1,2-dimethoxyethane (1 L), water (500 mL). Nitrogen was bubbled through the reaction mixture for 15 minutes. Tetrakis (triphenylphosphine) palladium (0) (15.2 g) was added to the reaction mixture and the resulting reaction mixture was heated to reflux and maintained at reflux overnight. The reaction mixture was cooled to room temperature and HCl (37%, 97 g) was added slowly. The reaction mixture separated and the product was extracted from the aqueous layer with ethyl acetate (EtOAc). The EtOAc layer was dried over $MgSO_4$, and concentrated under vacuum to provide viscous oil. The oil was slurried in a mixture of EtOAc and hexane (70/30 volume ratio) and the resulting solid was filtered to provide 170 g of product. Approximately one-half of the product was further slurried in the mixture of EtOAc and hexane (70/30 volume ratio), and then filtered and washed with dichloromethane to provide a yellow solid (40 g). The purified product was used as is for next step.

Step 2

Into a 250 mL reaction flask was added the product of Step 1, (4.0 g), 1,1-bis(4-methoxyphenyl)-2-propyn-1-ol (2.43 g), and chloroform (125 mL). To the resulting reaction mixture was added 0.25 grams of PPTS (pyridinium p-toluene-sulfonate). The reaction mixture was stirred at room temperature for 2 hours and further additions of 1,1-bis(4-methoxyphenyl)-2-propyn-1-ol (0.25 g) and PPTS (0.05 g) were made. The reaction mixture was stirred for another 2 hours and then washed with 200 mL of a 1:1 mixture of saturated aqueous $NaHCC_3$ and water. After the resulting layers separated, the organic layer was recovered, dried over anhydrous sodium sulfate and concentrated by rotary evaporation. The resulting residue was purified by slurrying in a 1:1 mixture of acetone and diethyl ether. An off-white solid resulted and was collected by filtration to yield 4.1 grams of product. NMR analysis showed the product to have a structure consistent with 3,3-di(4-methoxyphenyl)-6,7-dimethoxy-1'-(4-trifluoromethyl)phenyl-13,13-dimethyl-3H,13H-indeno[2',3':3,4] naphtho[1,2-b]pyran.

Example 2

Step 1

Into a suitable reaction flask was added 2,3-dimethoxy-7,7-dimethyl-9-bromo-7H-benzo[C]fluoren-5-ol (13.3 g), 3,5-bis(trifluoromethyl)phenylboronic acid (12.0 g), $K_2CC_3$ (14.0 g), triphenylphosphine (3.4 g), 1,2-dimethoxyethane (400 mL), and water (200 mL). Nitrogen was bubbled through the reaction mixture for 10 minutes. Palladium II acetate (0.56 g) was added to the reaction mixture and the initially orange colored solution turned dark before becoming orange upon heating to reflux. After 3 hours of heating, the reaction was cooled to room temperature and the aqueous phase separated. The recovered organic phase was diluted with dichloromethane and washed twice with brine before drying over MgSO$_4$ and evaporating the solvent. The resulting residue was chromatographed on a short silica gel column, eluting with 10% EtOAc in dichloromethane. Product containing fractions were combined and evaporated until the product began to crystallize. Hexane was added and the resulting solid was collected by filtration to give 16.5 g of tannish brown solid. This solid was used as is for the next reaction.

Step 2

The product of Step 1 (6 g) and 1,1-bis(4-methoxyphenyl)-2-propyn-1-ol (4 g) were combined in a round bottom flask and dissolved in chloroform (150 mL). To this solution, PPTS (0.15 g) was added. The reaction turned dark immediately and was heated to reflux for 2 hours. The solution was cooled to room temperature before being applied directly to a silica gel column. Product containing fractions were combined and concentrated until crystallization began. A portion of hexanes was then added to further induce crystallization. The product (5.0 g) was collected by filtration. NMR analysis showed the product to have a structure consistent with 3,3-di(4-methoxyphenyl)-6,7-dimethoxy-11-(3,5-bis(trifluoromethyl)phenyl)-13,13-dimethyl-3H,13H-indeno[2',3':3,4]naphtho[1,2-b]pyran.

Example 3

Step 1

Into a 1 L reaction flask was added 1-(4-bromophenyl)-2-methoxycarbonyl-4-hydroxy-6,7-dimethoxynaphthalene (45 g) produced by following Steps 1-3 of Example 1, in U.S. Patent Publication 2006-0228557, which disclosure is incorporated herein by reference, except that the acetoxy group of the product of Step 3 (1-(4-bromophenyl)-2-methoxycarbonyl-4-acetoxy-6,7-dimethoxynaphthalene) was converted to hydroxy using standard methanolysis conditions (refluxing for one hour in methanol containing 10% (volume to volume) concentrated (12M) hydrochloric acid); dimethoxyethane (300 mL) and water (100 g) followed by the addition of 2-trifluoromethylphenyl boronic acid (25 g) and Na$_2$CC$_3$ (23 g). Nitrogen was bubbled through the resulting slurry for 15 minutes. Tetrakistriphenyl phosphine palladium (0) (4 g) was added to the reaction mixture and heated to reflux. After about 5-6 hours, the reaction was cooled to room temperature and water (50 mL) was added. The solution pH was adjusted to 5.0 by addition of HCl (37%, 40 g). After the layers separated the organic layer was collected. The aqueous layer was extracted with EtOAc (2 times, 50 mL each time). The organic layers were combined, dried over anhydrous MgSO$_4$, and concentrated under vacuum to yield product containing methyl 4-hydroxy-6,7-dimethoxy-1-(2'-(trifluoromethyl)-[1,1'-biphenyl]-4-yl)-2-naphthoate, (70 g). The product was used for next step without purification.

Step 2

Ethyl magnesium chloride (EtMgCl) (20% by weight in dry tetrahydrofuran (dTHF), 210 mL) was added to a 1 L reaction flask under nitrogen. The product of Step 1 (17.5% by weight in dTHF, 200 mL) was added to reaction mixture over 40 minutes at room temperature. The reaction was exothermic and reaction temperature rose to 35° C. Upon completion of the addition, the resulting reaction mixture was stirred for 2 hours. More EtMgCl (20% by weight in dTHF, 75 mL,) was added to mixture. After one hour, the resulting mixture was poured into an aqueous 10 weight percent HCl solution. After the layers separated the organic layer was collected. The aqueous layer was extracted with EtOAc (2 times, 40 mL each time). The organic layers were combined, dried over anhydrous MgSO$_4$, and concentrated under vacuum to yield a product containing 3-(3-hydroxypentan-3-yl)-6,7-dimethoxy-4-(2'-(trifluoromethyl)-[1,1'-biphenyl]-4-yl)naphthalen-1-ol (34 g). The product was used for next step as it is.

Step 3

The product of Step 2 (34 g) was added to xylene (400 mL) in a 500 mL reaction flask, followed by addition of DBSA (dodecylbenzenesulfonic acid, 4 g). The reaction mixture was heated to reflux and maintained at reflux over night. Solvent was removed to yield unpurified product (39 g). The product was purified by column chromatography (EtOAc/hexanes, 1/3, volume ratio) to yield 10 g of product. NMR analysis showed the product to have a structure consistent with 7,7-diethyl-2,3-dimethoxy-9-(2-(trifluoromethyl)phenyl)-7H-benzo[c]fluoren-5-ol.

Step 4

Into a 100 mL reaction flask was added, the product of Step 3 (0.2 g dissolved in 40 mL of dichloromethane, PPTS (0.2 g) and 1,1-bis(4-methoxyphenyl)-2-propyn-1-ol (1 g). The resulting reaction mixture was stirred at room temperature for 4 hours. The solvent was removed by evaporation to provide 2.9 grams of unpurified product. The product was purified by column chromatography using EtOAc/hexanes, 1/3, volume ratio to yield 1.5 g of product. NMR analysis showed the product to have a structure consistent with 3,3-bis(4-methoxyphenyl)-6,7-dimethoxy-11-(2-trifluoromethyl)phenyl-13,13-diethyl-3H,13H-indeno[2',3':3,4]naphtho[1,2-b]pyran Example 4

Into a 250 mL dry reaction flask was added piperidine (0.95 grams) and 100 mL of dTHF. The mixture was stirred under a nitrogen atmosphere at room temperature. n-Butyl lithium (BuLi) (4.5 mL of 2.5 M in hexanes) was added dropwise to the reaction mixture over a 5-minute period. The reaction mixture became warm and a little cloudy. The product of Example 1 (4.0 g) was added in portions over a 5-minute period to the reaction mixture. The color of the reaction mixture turned deep brown. The resulting solution was stirred at room temperature for 2 hours. After cooling to room temperature, the reaction mixture was poured into 200 mL of saturated NaCl solution. Extraction was done with two 200 mL portions of EtOAc. The recovered organic layers were combined and washed with saturated NaCl solution (300 mL) followed by drying over anhydrous sodium sulfate. The solvents were removed by rotary evaporation to yield brown oil that foamed upon drying. The brown oil was purified by column chromatography (20% EtOAc in hexanes as the eluant). The fractions were collected, combined, evaporated, and dried under vacuum to recover 2.68 grams of product which was crystallized from ether to obtain a light yellow solid product. NMR analysis showed the product to have a structure consistent with 3,3-di-(4-methoxyphenyl-6-methoxy-7- piperidino-11-(4-trifluoromethyl)phenyl-13,13-dimethyl-3H,13H-indeno[2',3':3,4]naphtho[1,2-b]pyran.

Example 5

Into a 500 mL reaction flask was added the product of Step 1 of Example 1 (10.0 g), 1(4-methoxyphenyl)-1-(4-morpholinophenyl)-2-propyn-1-ol (7.66 g) and chloroform (250 mL). To the reaction mixture was added PPTS (0.54 g) and the resulting reaction mixture was stirred at room temperature overnight. Afterwards, 1(4-methoxyphenyl)-1-(4-morpholinophenyl)-2-propyn-1-ol (0.70 g) and PPTS (0.05 g) were added and the reaction mixture was stirred for another 2 hours. The resulting reaction mixture was washed with 400 mL of a 1:1 mixture of saturated aqueous NaHCC$_3$ and water. The recovered organic layer was dried over anhydrous sodium sulfate and concentrated by rotary evaporation. The resulting residue was purified by slurrying in diethyl ether. A greenish solid formed and was collected by vacuum filtration to yield 16.2 grams of product. NMR analysis showed the product to have a structure consistent with 3-(4-methoxyphenyl)-3-(4-morpholinophenyl)-6,7-dimethoxy-11-(4-trifluoromethyl)phenyl-13,13-dimethyl-3H,13H-indeno[2',3':3,4]naphtho[1,2-b]pyran.

Example 6

Into a 250 mL dry reaction flask was added piperidine (1.1 g) and 120 mL of dTHF. The resulting mixture was stirred under a nitrogen atmosphere at room temperature. BuLi (5.2 mL of 2.5 M in hexanes) was added dropwise to the reaction mixture over a 5-minute period. The reaction mixture became warm and a little cloudy. The product of Example 3 (5.0 g) was added in portions over a 5-minute period to the reaction mixture. The color of the reaction mixture turned deep reddish brown. The resulting solution was stirred at room temperature for 2 hours. The reaction mixture was poured into 300 mL of saturated NaCl solution. Extraction was done with two 250 mL portions of EtOAc. The organic layers were combined and washed with saturated NaCl solution (400 mL) followed by drying over anhydrous sodium sulfate. The solvents were removed by rotary evaporation to yield reddish brown oil that foamed upon drying. The product was purified by column chromatography (a mixture of hexane (40%), methylene chloride (50%) and EtOAc (10%) as the starting eluant). The fractions were combined, rotovaped, and dried under vacuum to obtain 3.25 grams of product. NMR analysis showed the product to have a structure consistent with 3-(4-methoxyphenyl)-3-(4-morpholinophenyl)-6-methoxy-7-piperidino-11-(4-trifluoromethyl)phenyl-13,13-dimethyl-3H,13H-indeno[2',3':3,4]naphtho[1,2-b]pyran.

Example 7

Into a 500 mL dry reaction flask was added morpholine (2.26 g) and 150 mL of dTHF. The reaction mixture was stirred under a nitrogen atmosphere at 0° C. BuLi (10.4 mL of 2.5 M in hexanes) was added dropwise to the reaction mixture over a 5-minute period. The reaction mixture became a little cloudy. The product of Example 3 (8.0 g) was added in portions over a 5-minute period to the reaction mixture. The color of the reaction mixture turned dark greenish gray. The cooling bath was removed and the resulting solution was stirred at room temperature for 2 hours. The reaction mixture was poured into 400 mL of saturated NaCl solution. Extraction was done with two 250 mL portions of EtOAc. The recovered organic layers were combined and washed with saturated NaCl solution (400 mL) followed by drying over anhydrous sodium sulfate. The solvents were removed by rotary evaporation to yield greenish gray oil that foamed upon drying. The material was purified by column chromatography (a mixture of hexane (40%), methylene chloride (30%) and EtOAc (30%) as the starting eluant). The fractions were combined, concentrated by rotary evaporation, and dried under vacuum to obtain greenish gray oil. This oil was dissolved in a minimum amount of diethyl ether and the resulting solution was cooled in the freezer overnight to get a yellow solid product. This solid was filtered and dried to obtain 5.87 grams of product. NMR analysis showed the product to have a structure consistent with 3-(4-methoxyphenyl)-3-(4-morpholinophenyl)-6-methoxy-7-morpholino-11-(4-trifluoromethyl)phenyl-13,13-dimethyl-3H,13H-indeno[2',3':3,4]naphtho[1,2-b]pyran.

Example 8

Step 1

Into a 1 liter reaction flask was added methylene chloride (500 mL), dihydroxybenzophenone (107 g) and 3,4-dihydro-2H-pyran (DHP, 105 g). The resulting mixture was cooled to about 5° C. in an ice bath. PPTS (1.0 g) was added and the reaction mixture was stirred 1.5 hours at 5° C. Triethylamine (1.0 g) was added and the mixture was stirred for an additional 10 min. The resulting mixture was filtered through basic alumina and concentrated to 219 g of residue by rotary evaporation. Heptanes (250 mL) were added, and the product solidified. The solid was isolated, washed with 200 mL heptanes and dried under vacuum to provide 175 g of the product bis(4-((tetrahydro-2H-pyran-2-yl)oxy)phenyl)methanone.

Step 2

The product of Step 1 (153 g) was added to a 1 L reaction flask with 230 mL dimethyl formamide (DMF). The mixture was cooled to 1° C. and was bubbled with acetylene gas for 20 min. A slurry of sodium acetylide (18% by weight in xylene/mineral oil from Aldrich, 215 g) was added all at once at 3° C. A brief exotherm to 11° C. was observed. After the reaction mixture was stirred in ice for 3.5 hrs, a 10 weight percent solution of NaCl was carefully added. During the phase separation, toluene (150 mL) was added. The recovered organic layer was washed with a 10 weight percent solution of NaCl (2 times with 145 mL each time). The resulting solution was filtered through a small alumina plug. The filtrate was concentrated by rotary evaporation to provide 227.5 g of product. NMR analysis showed the product to have a structure consistent with 1,1-bis[4-((ditetrahydro-2H-pyran-2-yl)oxy)phenyl]-2-propyn-1-ol.

Step 3

The product of Step 2 (7.2 g) and the product of Step 1 of Example 2 (7.5 g) were combined in a round bottom flask and dissolved in chloroform (130 mL). To this solution, PPTS (a catalytic amount ~200 mg) was added. The reaction was heated to reflux. After 5 hours of heating, methanol (25 mL) and an additional 200 mg portion of PPTS were added. Product began to precipitate out and was allowed to settle overnight. The fine precipitate was collected via vacuum filtration. The precipitate was re-suspended in a 1:1 mixture of acetone and methanol and heated to near reflux. The precipitate was allowed to settle overnight before again being collected by filtration to yield a beige solid product which was dried under vacuum. NMR analysis showed the product to have a structure consistent with 3,3-di(4-hydroxyphenyl)-6,7-dimethoxy-11-(3,5-bis(trifluoromethyl))phenyl-13,13-dimethyl-3H,13H-indeno[2',3':3,4]naphtho[1,2-b]pyran.

Example 9

Into a 250 mL dry reaction flask was added morpholine (0.97 g) and 120 mL of dTHF. The mixture was stirred under a nitrogen atmosphere at room temperature. BuLi (4.5 mL of 2.5 M in hexanes) was added dropwise to the reaction mixture over a 5-minute period. The reaction mixture became warm and a little cloudy. The product of Example 1 (4.0 g) was added in portions over a 5-minute period to the reaction mixture. The color of the reaction mixture turned deep brown. The resulting solution was stirred at room temperature for 2 hours. BuLi (1 mL of 2.5 M in hexanes) was added to the reaction mixture and stirred for another 2 hours. The reaction mixture was poured into 200 mL of saturated NaCl solution. Extraction was done with two 200 mL portions of EtOAc. The recovered organic layers were combined and washed with saturated NaCl solution (300 mL) followed by drying over anhydrous sodium sulfate. The solvents were removed by rotary evaporation to yield brown oil that foamed upon drying. This material was purified by crystallization from ether to obtain 3.40 grams of a light yellow solid product. NMR analysis showed the product to have a structure consistent with 3,3-di-(4-methoxyphenyl-6-methoxy-7-morpholino-11-(4-trifluoromethyl)phenyl-13,13-dimethyl-3H,13H-indeno[2',3':3,4]naphtho[1,2-b]pyran.

Example 10

Step 1

Into a 1 liter reaction flask was added 2,3-dimethoxy-7,7-dimethyl-9-bromo-7H-benzo[C]fluoren-5-ol (20 grams) the product of Step 5 of Example 1 in U.S. Patent Publication 2006-0228557, 1,1-bis(4-methoxyphenyl)-2-propyn-1-ol (14.14 grams, 1.05 equivalents) and chloroform (125 mL) To this was added PPTS (0.63 grams, 0.05 equivalents) and the reaction mixture was stirred at room temperature for 2 hours. The reaction mixture was then washed with 400 mL of a 1:1 mixture of saturated aqueous NaHCO₃ and water. The layers separated and the recovered organic layer was dried over anhydrous sodium sulfate and concentrated by rotary evaporation. The resulting residue was purified by slurrying in diethyl ether. An off-white solid resulted and was collected by filtration to yield 31.1 of product. NMR analysis showed the product to have a structure consistent with 3,3-di(4-methoxyphenyl)-6,7-dimethoxy-11-bromo-13,13-dimethyl-3H,13H-indeno[2',3':3,4]naphtho[1,2-b]pyran.

Step 2

The product of Step 1 (10 g) was added to a 1 L reaction flask containing dimethoxyethane (200 mL) and water (100 mL), followed by addition of 2-trifluoromethylphenyl boronic acid (3.5 g) and Na₂CC₃ (3.3 g). Nitrogen was bubbled through the resulting slurry for 15 minutes. Tetrakistriphenyl phosphine palladium (0) (0.6 g) was added to reaction mixture and heated to reflux. After about 5-6 hours, the reaction was cooled to room temperature and water (30 mL) was added. The solution pH was adjusted to 5 by addition of HCl (37%, 8 g). After the layers separated, the organic layer was collected. The aqueous layer was extracted with EtOAc (2 times, 30 mL each time). The organic layers were combined, dried over anhydrous MgSO₄, and concentrated under vacuum to yield unpurified product (12 g). The product was purified by column chromatography (EtOAc/Hexanes, 1/3, volume ratio) to yield 3,3-bis(4-methoxyphenyl)-6,7-dimethoxy-11-(2-trifluoromethyl)phenyl-13,13-dimethyl-3H,13H-indeno[2',3':3,4]naphtho[1,2-b]pyran (8 g).

Step 3

Morpholine (0.7 g) was dissolved in dTHF (40 mL) in a 100 mL reaction flask. BuLi (2.5 M in hexanes, 2.7 mL) was added slowly. The resulted solution was stirred at room temperature for 30 minutes and the product of Step 1 (1.6 g) was added slowly to the reaction mixture. After 1 hour of stirring at room temperature, morpholine (0.45 g) and BuLi (1.8 mL) were added to the reaction mixture in that order. After 30 minutes, the reaction was poured into water (50 mL). The product was extracted with EtOAc (2 times with 10 mL each time). The recovered organic layers were combined, dried over anhydrous MgSO₄, and concentrated under vacuum to provide product (2.0 g). The product was purified by column chromatography (EtOAc/Hexanes, 1/3, volume ratio). The fractions were concentrated and the solid was slurried in methanol (MeOH). The slurry was filtered via a fritted filter and washed with MeOH (3 times each time with 20 mL) to provide 1.1 g of a grey solid product. NMR analysis showed the product to have a structure consistent with 3,3-bis(4-methoxyphenyl)-6-methoxy-7-morpholino-11-(2-trifluoromethyl)phenyl-13,13-dimethyl-3H,13H-indeno[2',3':3,4]naphtho[1,2-b]pyran.

Example 11

Step 1

Into a 1 L reaction flask containing acetic anhydride (600 mL) was added 7,7-dimethyl-7H-benzo[c]fluoren-5-ol (150 g) followed by the addition of, 4-dimethylaminopyridine (DMAP) (0.2 g). The reaction mixture was heated to 130° C. and maintained at this temperature for 2 to 3 hours. The resulting reaction mixture was cooled to 120° C. and maintained at this temperature overnight and then cooled to room temperature prior to being poured into ice water and stirred for 2 hours. An off-white solid formed and was collected by filtration. The recovered solid was washed with water, and then with MeOH/water (v/v, 50/50). The product was air-dried to yield 175 g solid and was used in the next step without further purification.

Step 2

Into a 1 L reaction flask containing 400 mL of DMF was added the product of Step 1 (120 g) followed by the addition of N-bromosuccinimide (NBS) (82 g). The reaction mixture was heated to 90° C., spiked to 120° C. briefly and returned to about 95° C. and was heated at this temperature for 4 hours. Additional NBS was added (8 g) and the reaction mixture was heated for 2 more hours. The resulting reaction mixture was poured into water and was extracted with EtOAc. The recovered organic layer was washed with water (3×200 mL), dried over MgSO₄ and concentrated under vacuum to provide product. The product was slurried in methanol and the solid was recovered by filtration, washed with methanol (3×200 mL) and dried to provide a light yellowish solid (107 g). The product was used in the next step without purification.

Step 3

Into a 1 L reaction flask containing MeOH (500 mL) was added the product of Step 2 (107 g) followed by the addition of conc. HCl, 37% (3 g). The reaction mixture was heated to reflux for 2 hours. The solvents were removed from the resulting reaction mixture to yield about 100 g solid. The recovered solid was slurried in about 250 mL dichloromethane (DCM)/Hexanes (v/v, 50/50) for 10 minutes at room temperature. The slurry was filtered and the recovered solid was washed with DCM/Hexanes (v/v, 5/5) to provide about 47 g of product. NMR analysis showed the product to have a structure consistent with 7,7-dimethyl-9-bromo-7H-benzo[c]fluoren-5-ol.

Step 4

The product of Step 3 (20 g) and 4-trifluoromethyl phenyl boronic acid (15.8 g) were added to a 1 L reaction flask containing a solution of dimethoxyethane (200 mL) and water (100 mL) followed by the addition of $Na_2CC_3$ (12.5 g). The resulting solution was bubbled with nitrogen for 10 minutes and then the palladium catalyst, Pd[PPh3]4, (3 g) was added to the reaction mixture. The reaction mixture was heated to reflux temperatures under a nitrogen atmosphere. The initially light greenish white solution turned dark upon heating. After 1 hour, the reaction mixture was cooled to room temperature and poured into 400 mL of water followed by extraction with ethyl acetate (2×300 mL). The organic layers were combined and washed with saturated NaCl solution (1×400 mL). This organic layer was dried over anhydrous sodium sulfate and concentrated by rotary evaporation to yield the product (23 g) which was used in the next step without purification.

Step 5

The product of Step 4 (4.0 g), 1-phenyl-1-(4-morpholinophenyl)-2-propyn-1-ol (3.47 g, 1.2 equivalents) and chloroform (120 mL) were combined in a 500 mL reaction flask. To this was added PPTS (0.25 g, 0.1 equivalents) and the reaction mixture was heated to 50° C. and maintained at this temperature for 4 hours. Added 1-phenyl-1-(4-morpholinophenyl)-2-propyn-1-ol (0.75 g) and heated the reaction mixture for another 1 hour. The reaction mixture was then washed with 400 mL of a 1:1 mixture of saturated aqueous $NaHCC_3$ and water. The organic layer was dried over anhydrous sodium sulfate and concentrated by rotary evaporation. The resulting residue was purified by column chromatography using a mixture of 60% hexane, 35% methylene chloride and 5% ethyl acetate as the starting eluant. The purple fractions were combined and rotovaped to obtain 4.6 grams of purple foam. NMR analysis show the purple product to have a structure consistent with 3-phenyl-3'-(4-morpholinophenyl)-11-(4-trifluoromethyl)phenyl-13,13-dimethyl-3H,13H-indeno[2',3':3,4]naphtho[1,2-b]pyran.

Example 12

Step 1

The product of Step 3 of Example 11, 7,7-dimethyl-9-bromo-7H-benzo[C]fluoren-5-ol (15 g) and 2-trifluoromethyl phenyl boronic acid (10.5 g) were added to a solution of dimethoxyethane (150 mL) and water (75 mL) in a 1 L reaction flask, followed by addition of $Na_2CC_3$ (9.4 g). The resulting solution was bubbled with nitrogen for 10 minutes and a palladium catalyst, Pd[PPh3]4, (2.5 g) was added to the reaction mixture. The reaction mixture was heated to reflux temperature under a nitrogen atmosphere. The initially light greenish white solution turned dark upon heating. After refluxing overnight, the reaction was cooled to room temperature and poured into 400 mL of water followed by extraction with ethyl acetate (2×300 mL). The organic layers were recovered, combined and washed with saturated NaCl solution (1×400 mL). The resulting organic layer was dried over anhydrous sodium sulfate and concentrated by rotary evaporation to yield the product (17.2 g). This material was not purified further and used in the next step.

Step 2

The product of Step 1 (3.0 g), 1-phenyl)-1-(4-morpholinophenyl)-2-propyn-1-ol (2.50 g, 1.15 equivalents) and dichloroethane (120 mL) were combined in a 500 mL reaction flask. To this mixture was added PPTS (0.56 g, 0.3 equivalents) and trimethyl orthoformate (1.6 g, 2 equivalents). The reaction mixture was heated to reflux and maintained at that temperature for 2 hours. The following materials were added to the reaction mixture: 1-phenyl-1-(4-morpholinophenyl)-2-propyn-1-ol (1.0 g), PPTS (0.2 grams of and 0.5 grams of trimethyl orthoformate and it was again to reflux temperature for another 2 hours. The reaction mixture was cooled to room temperature and washed with 100 mL of a 1:1 mixture of saturated aqueous $NaHCC_3$ and water. The organic layer was dried over anhydrous sodium sulfate and concentrated by rotary evaporation. The resulting residue was purified using 20% ethyl acetate/80% hexanes (v/v) by chromatography to obtain 4.4 grams of a blue solid. Precipitation from diethyl ether yielded a white solid. The pure product was filtered, washed with diethyl ether and then dried under vacuum to obtain 2.80 grams of a bluish white solid. NMR analysis showed the product to have a structure consistent with 3-(4-morpholinophenyl)-3-phenyl-11-(2-trifluoromethyl)phenyl-13,13-dimethyl-3H,13H-indeno[2',3':3,4]naphtho[1,2-b]pyran.

Example 13

Step 1

Into a suitable reaction flask was added 2,3-dimethoxy-7,7-dimethyl-9-bromo-7H-benzo[C]fluoren-5-ol (6.5 g), 4,4,5,5-tetramethyl-1,3,2-dioxaborolane (5.4 g), potassium acetate (6.9 g) and a palladium catalyst, Pd(dppf)$Cl_2$, (0.75 g) in dry triethylamine (100 mL). The solution was purged with nitrogen for 10 minutes and then stirred at 80° C. overnight. The solvent was removed and the resulting residue was extracted with ethyl acetate and water. The recovered organic phase was dried with sodium sulfate and subject to column chromatography using 30% ethyl acetate/hexanes as eluant to provide 7.25 grams of product. NMR analysis showed the product to have a structure consistent with 2,3-dimethoxy-7,7-dimethyl-9-(4,4,5,5-tetramethyl-1,3,2-dioxaborolan-2-yl)-7H-benzo[C]fluoren-5-ol.

Step 2

The product of Step 1 (1.0 g), 2-bromo-3-(trifluoromethyl) pyridine (0.5 g), potassium carbonate (0.5 g), palladium acetate (0.04 g), triphenylphosphine (0.1 g), 1,2-dimethoxyethane (40 mL), and water (20 mL) were combined in a 200 mL reaction flask. Nitrogen was bubbled through the reaction mixture for 10 minutes. The solution was stirred at 80° C. overnight. The resulting reaction mixture was cooled to room temperature and the aqueous phase separated. The recovered organic phase was diluted with dichloromethane and washed twice with brine before drying over $Na_2SO_4$ and evaporating the solvent. The resulting residue was chromatographed on a short silica gel column, eluting with 30% EtOAc in hexanes to provide 0.4 g of product. This solid was used as is for the next reaction.

Step 3

The product of Step 2 (0.14 g), 1,1-bis(4-methoxyphenyl)-2-propyn-1-ol (0.12 g) and chloroform (15 mL) were combined in a 50 mL reaction flask. To this mixture, PPTS was added (0.05 g). The reaction mixture was stirred at room temperature overnight. The solvent was removed before purifying the residue by column chromatography on silica gel. Product containing fractions were combined and the product was recrystallized from dichloromethane/ethanol mixture to provide 0.17 g of product as yellow crystals. NMR analysis showed the product to have a structure consistent with 3-(4-butoxyphenyl)-3-(4-methoxyphenyl)-6,7-dimethoxy-11-(3-(trifluoromethyl)pyridin-2-yl)-13,13-dimethyl-3H,13H-indeno[2',3':3,4]naphtho[1,2-b]pyran.

Comparative Example 1

2,3-Dimethoxy-7,7-dimethyl-9-phenyl-7H-benzo[C]fluoren-5-ol (10 g) was added to chloroform (200 mL) in a 500 mL reaction flask followed by the addition of PPTS (0.6 g) and 1,1-bis(4-methoxyphenyl)-2-propyn-1-ol (7.1 g). After two hours of stirring at room temperature, PPTS (0.6 g) was added. After an additional 30 minutes of stirring, 1,1-bis(4-methoxyphenyl)-2-propyn-1-ol (1.2 g) was added. After hour of stirring, 1,1-bis(4-methoxyphenyl)-2-propyn-1-ol (1.5 g) was added. The resulting reaction mixture was stirred for 2 hours at room temperature and PPTS (0.6 g) was added. After about 16 hours, a saturated aqueous solution of NaHCC₃ (80 mL) was added. The layers separated and the organic layer was recovered. The aqueous layer was extracted with dichloromethane (2 times, 50 mL each time). The organic layers were combined, dried over anhydrous MgSO₄, and concentrated under vacuum to yield unpurified product (30 g). The product was slurried over acetone/diethyl ether (Et2O) (55 mL, 25/75, volume ratio). The recovered solid was isolated and washed with acetone/Et2O (25/75, volume ratio, 2 times, 15 mL each time). About 9 g product was recovered. NMR analysis showed the product to have a structure consistent with 3,3-bis(4-methoxyphenyl)-6,7-dimethoxy-11-phenyl-13,13-dimethyl-3H,13H-indeno[2',3':3,4]naphtho[1,2-b]pyran.

Comparative Example 2

3,3-Di(4-methoxyphenyl)-6,7-dimethoxy-11-(4-fluorophenyl)-13,13-dimethyl-3H,13H-indeno[2',3':3,4]naphtho[1,2-b]pyran was prepared by the procedure of Example 5 of U.S. Patent Publication 2006-0228557.

Comparative Example 3

3,3-Di(4-methoxyphenyl)-10,11-dimethoxy-13,13-dimethyl-3H,13H-indeno[2',3':3,4]naphtho[1,2-b]pyran was prepared by the procedure of Example 4 of U.S. Pat. No. 6,296,785.

Comparative Example 4

Piperidine (2.4 g) was dissolved in dTHF (150 mL) in a 500 mL reaction flask. BuLi (11.2 mL, 2.5 M in hexanes) was added slowly. The resulting solution was stirred at room temperature for 30 minutes and 3-(4-morpholinophenyl)-3-(4-methoxyphenyl)-6,7-dimethoxy-11-phenyl-13,13-dimethyl-3H,13H-indeno[2',3':3,4]naphtho[1,2-b]pyran (9.0 g) was added slowly to the reaction mixture. After 1.5 h stirring at room temperature, more BuLi (5 mL) was added. The reaction was exothermic and temperature went up to 24° C. from 21° C. The reaction was stirred for two more hours and poured into a brine solution. The layers separated and the organic layer was collected. The aqueous layer was extracted with dichloromethane (2 times, 30 mL each time). The organic layers were combined, dried over anhydrous MgSO₄, and concentrated under vacuum to yield unpurified product (9.5 g). The product was purified by column chromatography (EtOAc/Hexanes, 3/2, volume ratio) to yield product 7 g. NMR analysis showed the product to have a structure consistent with 3,3-bis(4-methoxyphenyl)-6-methoxy-7-piperidino-11-phenyl-13,13-dimethyl-3H,13H-indeno[2',3':3,4] naphtho[1,2-b]pyran.

Comparative Example 5

2,3-Dimethoxy-7,7-dimethyl-9-phenyl-7H-benzo[C]fluoren-5-ol, 10 g was added to dichloromethane (200 mL) in a 500 mL reaction flask followed by the addition of PPTS (0.6 g) and 1-(4-methoxyphenyl)-1-(4-morpholinophenyl)-2-propyn-1-ol (8.6 g). After one hour of stirring at room temperature, PPTS (0.6 g) was added. The reaction mixture was stirred at room temperature for about 60 hours and a saturated aqueous solution of NaHCC₃ (80 mL) was added. The layers separated and the organic layer was recovered. The aqueous layer was extracted with dichloromethane (2 times, 50 mL each time). The organic layers were combined, dried over anhydrous MgSO₄, and concentrated under vacuum to yield unpurified product (23 g). The product was slurried over acetone/Et2O/hexanes (100 mL, Oct. 10, 1990, volume ratio). The resulting solid was isolated and washed with acetone/hexane (10/90, volume ratio, 2 times, 50 mL each time) to yield about 16.7 g product. NMR analysis showed the product to have a structure consistent with 3-(4-morpholinophenyl)-3-(4-methoxyphenyl)-6,7-dimethoxy-11-phenyl-13,13-dimethyl-3H,13H-indeno[2',3':3,4]naphtho[1,2-b]pyran.

Comparative Example 6

Step 1

Piperidine (11.6 grams, 2.7 eq.) was weighed into a 500 mL dry reaction flask. dTHF (150 mL) was added to the reaction flask and stirred under a nitrogen atmosphere at room temperature. BuLi (50.5 mL (2.5 eq.) of 2.5 M in hexanes) was added dropwise to the reaction mixture over a 5-minute period. The reaction mixture became warm and a little cloudy. 2,3-Dimethoxy-7,7-dimethyl-9-phenyl-7H-benzo[C]fluoren-5-ol (20.0 g) was added in portions over a 10-minute period to the reaction mixture. The resulting solution was stirred at 40° C. for 2 hours. Piperidine (1.2 g) and then 5 mL of BuLi (2.5 M in hexanes) was added dropwise to the reaction mixture over a 5-minute period. The resulting solution was stirred at 40° C. for another 2 hours. After cooling to room temperature, the reaction mixture was poured into 400 mL of saturated NaCl solution and neutralized carefully with 10% HCl until pH~=7. Extraction was done with two 250 mL portions of EtOAc. The organic layers were combined and washed with saturated NaCl solution (1×400 mL) followed by drying over anhydrous sodium sulfate. The solvent was removed by rotary evaporation to yield an off white solid. This material was purified by slurrying in diethyl ether. The resulting product was filtered off and dried under vacuum to yield 17.7 grams of the primary product, 2-piperidino-3-dimethoxy-7,7-dimethyl-9-phenyl-7H-benzo[C]fluoren-5-ol and (3.95 grams) of a secondary product.

Step 2

The primary product of Step 1 (20.0 g) was weighed into a 500 mL reaction flask and toluene (154 mL) was added. DBSA (0.73 g., 0.05 equivalents) was added. The reaction mixture was heated to 75° C. and stirred under a nitrogen atmosphere. A solution of 1-(4-methoxyphenyl)-1-(4-morpholinophenyl)-2-propyn-1-ol (17.26 g., 1.2 eq.) in toluene (77 mL) was added drop wise to the reaction flask over a 1 hour period. The reaction mixture was stirred at 75° C. After 4 hours, 1-(4-methoxyphenyl)-1-(4-morpholinophenyl)-2-propyn-1-ol (5 g) was added and the resulting mixture was stirred at 75° C. After about 16 hours, 1-(4-methoxyphenyl)-1-(4-morpholinophenyl)-2-propyn-1-ol (2.5 g) and PPTS (0.5 g) were added and the reaction mixture was heated for another 4 hours. The reaction mixture was cooled to room temperature, diluted with 250 mL of EtOAc, and washed with 400 mL of a 1:1 mixture of saturated aqueous NaHCC$_3$ and water. The layers separated and the recovered organic layer was dried over anhydrous sodium sulfate and concentrated by rotary evaporation. The resulting material was purified by column chromatography (50% hexanes, 40% methylene chloride and 10% EtOAc as the starting eluant) and the photochromic fractions were combined, concentrated by rotary evaporation, and dried under vacuum to yield 21 grams of purplish foam. This foam was further purified by crystallization from diethyl ether to obtain an off white solid. NMR analysis show the product to have a structure consistent with 3-(4-methoxyphenyl)-3-(4-morpholinophenyl)-6-dimethoxy-7-piperidino-11-phenyl-13,13-dimethyl-3H,13H-indeno[2',3':3,4]naphtho[1,2-b]pyran.

Comparative Example 7

Morpholine (3.5 g) was dissolved in dTHF (80 mL) in a 250 mL reaction flask. BuLi (1.6 M in hexanes, 10 mL) was added slowly. The resulted solution was stirred at room temperature for 30 minutes and the product of CE-5,3-(4-morpholinophenyl)-3-(4-methoxyphenyl)-6,7-dimethoxy-11-phenyl-13,13-dimethyl-3H,13H-indeno[2',3':3,4]naphtho[1,2-b]pyran (3.5 g) was added slowly to the reaction mixture. The reaction was gently warmed for one hour. The resulting reaction mixture was cooled to room temperature and poured into a brine solution. The layers were separated and the organic layer was collected. The aqueous layer was extracted with dichloromethane (2 times, 30 mL each time). The organic layers were combined, dried over anhydrous MgSO$_4$, concentrated under vacuum and purified by column chromatography (EtOAc/Hexanes, 3/2, volume ratio) to give product 1.3 g. NMR analysis show the product to have a structure consistent with 3,3-bis(4-methoxyphenyl)-6,7-dimethoxy-11-(2-trifluoromethylphenyl)-13,13-dimethyl-3H,13H-indeno[2%3':3,4]naphtho[1,2-b]pyran.

Comparative Example 8

2,3-Dimethoxy-7,7-dimethyl-9-phenyl-7H-benzo[C]fluoren-5-ol (1.7 g) and 1,1-bis[4-((ditetrahydro-2H-pyran-2-yl)oxy)phenyl]-2-propyn-1-ol (2.15 g) were added to dichloromethane (200 mL) in a 500 mL flask followed by the addition of PPTS (60 mg) to the reaction mixture. The resulting solution was stirred at room temperature. After about 16 hours, MeOH (10 mL) and PPTS (60 mg) were added to the reaction mixture. The product was insoluble and isolated by filtration and treated with PPTS (0.2 g) in ethanol/acetone (1/5, volume ratio) at room temperature for about 64 hours. The resulting off-white solid product (0.83 g) was isolated. NMR analysis show the product to have a structure consistent with 3,3-bis(4-hydroxyphenyl)-6,7-dimethoxy-11-phenyl-13,13-dimethyl-3H,13H-indeno[2',3':3,4]naphtho[1,2-b]pyran.

Comparative Example 9

Step 1

A solution of morpholine (27.8 mL) in dTHF (600 mL) was added to a 2 L reaction flask under nitrogen. Methyl lithium (1.4 M in diethyl ether, 223 mL) was added over 20 minutes at 0° C. The resulting mixture was stirred for 30 mins at 0° C. and then warmed to room temperature and stirred for 20 min. A solution of 2,3-dimethoxy-7,7-dimethyl-7H-benzo[C]fluoren-5-ol (20 g) in dTHF (300 mL) was added to the reaction mixture over an interval of 30 minutes. The resulting reaction was heated to reflux. After heating for 1.5 hours at reflux, the reaction was cooled to room temperature and stirred for about 16 hours. The resulting reaction mixture was poured to ice water and the layers were separated. The aqueous layer was extracted with EtOAc (4 times with 100 mL each time). The combined organic layers were dried over anhydrous MgSO$_4$ and concentrated to yield a dark brown oil. The dark oil was crystallized from a mixture of Hexanes/EtOAc (3:1, volume ratio) to yield 17.9 g of a powder. NMR analysis showed the product to have a structure consistent with 2-morpholino-3-methoxy-7,7-dimethyl-7H-benzo[C]fluoren-5-ol.

Step 2

The product of Step 1 (5 g) was added to dichloromethane (100 mL) in a 250 mL reaction flask, followed by addition of 1,1-bis(4-methoxyphenyl)-2-propyn-1-ol (2 g). The reaction was stirred at room temperature for 16 hours and then poured into a 5 weight percent aqueous solution of NaHCC$_3$. The layers separated and the resulting organic layer was recovered and the aqueous layer was extracted with dichloromethane (2 times with 20 mL each time). The organic layers were combined, dried over anhydrous MgSO$_4$ and concentrated to provide 6.3 g of product. The product was purified by column chromatography [EtOAc/Hexanes, 1/3, volume ratio] to provide 2.4 g of product. NMR analysis showed the product to have a structure consistent with 3,3-bis(4-methoxyphenyl)-6-methoxy-7-morpholino-13,13-dimethyl-3H,13H-indeno[2',3':3,4]naphtho[1,2-b]pyran.

Comparative Example 10

The product of Step 3 of Example 11, 7,7-dimethyl-9-phenyl-7H-benzo[C]fluoren-5-ol (2.0 g) was dissolved in chloroform (125 mL) in a 500 mL reaction flask. To this was added p-toluene sulfonic acid (PTSA) (0.2 g). The reaction was stirred at 50° C. under nitrogen. Over a 30 minute interval, portions of 1-phenyl-1-(4-morpholinophenyl)-2-propyn-1-ol (1.74 g) were added to the reaction mixture. The resulting reaction mixture was stirred at 50° C. for 2 hours. The reaction mixture was cooled to room temperature, washed with 100 mL of a saturated aqueous NaHCC$_3$ solution, and extracted with chloroform. The recovered organic layers were combined, dried over MgSO$_4$ and concentrated under vacuum. The product was purified by chromatography to yield 1.6 grams of a product that was treated with diethyl ether to yield an off-white solid (1.2 g). NMR analysis showed the product to have a structure consistent with 3-(4-phenyl)-3'-(4-morpholinophenyl)-11-phenyl-13,13-dimethyl-3H,13H-indeno[2',3':3,4]naphtho[1,2-b]pyran.

Part 2

Photochromic Performance Testing

The photochromic performance of the photochromic materials of Examples 1-13 and Comparative Examples (CE) 1-10 were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part polyethylene glycol) 600 dimethacrylate, and 0.033 weight percent 2,2'-azobis(2-methyl propionitrile) (AIBN). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a utility knife to score the surface and snap into 2 inch (5.1 cm) test squares.

The photochromic test squares prepared as described above were tested for photochromic response on an optical bench. Nor to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max-vis}$ is the wavelength in the visible spectrum at which the maximum absorption of the activated-state form of the photochromic compound in a test square occurs. The $\lambda_{max-vis}$ wavelength was determined by testing the photochromic test squares in a Varian Cary 300 UV-Visible spectrophotometer; it may also be calculated from the spectrum obtained by the S2000 spectrometer on the optical bench.

The saturated optical density ("Sat'd OD") for each test square was determined by opening the shutter from the xenon lamp and measuring the transmittance after exposing the test chip to 3 W/m2 UVA radiation for 30 minutes. The $\lambda_{max-vis}$ at the Sat'd OD was calculated from the activated data measured by the S2000 spectrometer on the optical bench. The First Fade Half Life ("$T_{1/2}$") or Bleach Rate is the time interval in seconds for the absorbance of the activated-state form of the photochromic material in the test squares to reach one half the Sat'd OD absorbance value at room temperature (23° C.), after removal of the source of activating light.

Part 3

Test Results

Results for the photochromic materials tested are listed below in Table 1.

TABLE 1

Photochromic Test Data

| Example | $\lambda_{max}$ (nm) Visible | Sat. OD | Bleach Rate $T_{1/2}$ (sec) |
|---|---|---|---|
| 1 | 448 | 1.25 | 163 |
| 2 | 458 | 0.91 | 171 |
| 3 | 456 | 0.93 | 134 |
| 13 | 457 | 1.06 | 184 |
| CE 1 | 453 | 1.15 | 243 |
| CE 2 | 452 | 1.09 | 238 |
| CE 3 | 451 | 1.27 | 236 |
| 4 | 482 | 1.59 | 276 |
| CE 4 | 482 | 1.99 | 338 |
| 5 | 481 | 0.54 | 148 |
| CE 5 | 479 | 0.68 | 197 |
| 6 | 507 | 1.08 | 232 |
| CE 6 | 504 | 1.41 | 299 |
| 7 | 499 | 0.93 | 191 |
| CE 7 | 497 | 0.91 | 249 |
| 8 | 460 | 0.84 | 114 |
| CE 8 | 459 | 0.94 | 155 |
| 9 | 474 | 1.36 | 242 |
| 10 | 473 | 1.65 | 248 |
| CE 9 | 471 | 1.68 | 348 |
| 11 | 592 | 1.21 | 182 |
| 12 | 587 | 1.27 | 200 |
| CE 10 | 592 | 1.36 | 248 |

Examples 1, 2 and 3 have the trifluoromethyl substituent(s) located at the 4-position, 3- and 5-positions and the 2-position of the phenyl at the 11-position of each compound, respectively. Example 13 has a trifluoromethyl substituent located at the 3-position of the pyridyl ring at the 11-position of the compound. This example also has a butoxy substituted phenyl at the 3 position which is expected to have very little, if any effect on the Bleach (T1/2) when compared to a methoxy substituted phenyl at the same position. Comparative Example (CE) 1 has an unsubstituted phenyl at the 11-position, CE-2 has a 4-fluorophenyl at the 11-position and CE-3 is unsubstituted at the 11-position. Examples 4-7 each have the trifluoromethyl located at the 4-position of the phenyl at the 11-position and CE-4-7 have an unsubstituted phenyl at the 11-position on each corresponding comparative example. Example 8 has trifluoromethyl groups located at the 3- and 5-positions and CE-8 has an unsubstituted phenyl at the 11-position. Example 9 has the trifluoromethyl at the 4-position and Example 10 has the trifluoromethyl at the 2-position of the phenyl at the 11-position. CE-9 is unsubstituted at the 11-position. Examples 11 and 12 have the trifluoromethyl substituent(s) located at the 4-position and the 2-position of the phenyl at the 11-position of each compound, respectively, and the 6- and 7-positions are unsubstituted. CE-10 has an unsubstituted phenyl at the 11-position and is also unsubstituted at the 6- and 7-positions. In each comparison, Examples 1-13 demonstrated a faster bleach rate (T1/2) than the corresponding Comparative Examples 1-10

Whereas particular embodiments of this invention have been described above for purposes of illustration, it will be evident to those skilled in the art that numerous variations of the details of the present invention may be made without departing from the invention as defined in the appended claims.

What is claimed is:
1. A photochromic material represented by graphic formulas I and II:

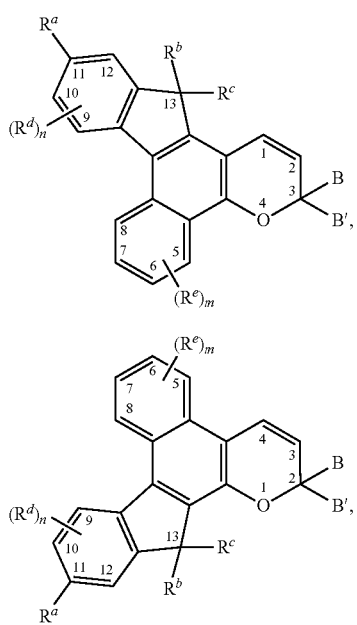

or a mixture thereof, wherein:
(i) $R^a$ is a pi-conjugation extending group bonded to the 11-position of said indeno-fused naphthopyran, said pi-conjugation extending group having at least one pendent halo-substituted group bonded thereto, said pi-conjugation extending group extending the pi-conjugation system of said indeno-fused naphthopyran, provided the 13-position of said indeno-fused naphthopyran is substantially free of spiro-substituents; wherein said pi-conjugation extending group is a group represented by —C($R_{30}$)=C($R_{31}$)($R_{32}$) or —C≡C—$R_{33}$, wherein $R_{30}$, $R_{31}$ and $R_{32}$ are each independently, amino, dialkyl amino, diaryl amino, acyloxy, acylamino, a substituted or unsubstituted $C_1$-$C_{20}$ alkyl, a substituted or unsubstituted $C_2$-$C_{20}$ alkenyl, a substituted or unsubstituted $C_2$-$C_{20}$ alkynyl, halogen, hydrogen, hydroxy, oxygen, a polyol residue, a substituted or unsubstituted phenoxy, a substituted or unsubstituted benzyloxy, a substituted or unsubstituted alkoxy, a substituted or unsubstituted oxyalkoxy, alkylamino, mercapto, alkylthio, a substituted or unsubstituted aryl, a substituted or unsubstituted heteroaryl, a substituted or unsubstituted heterocyclic group, provided that at least one of $R_{30}$, $R_{31}$ and $R_{32}$ is said pendent halo-substituted group, and $R_{33}$ is said pendent halo-substituted group; or
said pi-conjugation extending group is selected from a substituted or unsubstituted aryl; and a substituted or unsubstituted heteroaryl;

(ii) n ranges from 0 to 3;
(iii) m ranges from 0 to 4;
(iv) each $R^d$ and $R^e$ is independently chosen for each occurrence from:
a reactive substituent; a compatiblizing substituent; hydrogen; $C_1$-$C_6$ alkyl; halo; $C_3$-$C_7$ cycloalkyl; a substituted or unsubstituted phenyl, said phenyl substituents being $C_1$-$C_6$ alkyl or $C_1$-$C_6$ alkoxy; —$OR^{10}$ or —OC(=O)$R^{10}$ wherein $R^{10}$ is S, hydrogen, amine, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl or mono($C_1$-$C_4$)alkyl substituted $C_3$-$C_7$ cycloalkyl; a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_t$— or —[O—(CH$_2$)$_t$]$_k$—, wherein t ranges from 2 to 6, and k ranges from 1 to 50, and wherein the substituent is connected to an aryl group on another photochromic material; —N($R^{11}$)$R^{12}$, wherein $R^{11}$ and $R^{12}$ are each independently hydrogen, $C_1$-$C_6$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, or $R^{11}$ and $R^{12}$ come together with the nitrogen atom to form a $C_3$-$C_{20}$ hetero-bicycloalkyl ring or a $C_4$-$C_{20}$ heterotricycloalkyl ring; a nitrogen containing ring represented by:

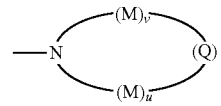

wherein each -M- is independently chosen for each occurrence from —CH$_2$—, —CH($R^{13}$)—, —C($R^{13}$)$_2$—, —CH(aryl)-, —C(aryl)$_2$- and —C($R^{13}$)(aryl)-, and -Q- is -M-, —O—, —S—, —S(O)—, —SO$_2$—, —NH—, —N($R^{13}$)— or —N(aryl)-, wherein each $R^{13}$ is independently $C_1$-$C_6$ alkyl, each (aryl) is independently phenyl or naphthyl, u ranges from 1 to 3, and v ranges from 0 to 3, provided that if v is 0, -Q- is -M-; a group represented by:

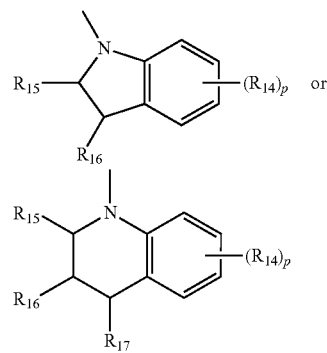

wherein each $R^{15}$, $R^{16}$ and $R^{17}$ is independently hydrogen, $C_1$-$C_6$ alkyl, phenyl or naphthyl, or $R^{15}$ and $R^{16}$ together form a ring of 5 to 8 carbon atoms, each $R^{14}$ is independently $C_1$-$C_6$ alkyl, $C_1$-$C_6$ alkoxy, halo, and p ranges from 0 to 3; and a substituted or unsubstituted $C_4$-$C_{18}$ spirobicyclic amine or a substituted or unsubstituted $C_4$-$C_{18}$ spirotricyclic amine, wherein said substituents are independently aryl, $C_1$-$C_6$ alkyl, $C_1$-$C_6$ alkoxy or phenyl($C_1$-$C_6$)alkyl; or an $R^e$ group in the 6-position and an $R^e$ group in the 7-position together form a group represented by:

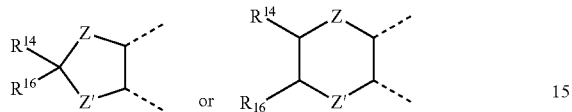

wherein each Z and Z' is independently oxygen or the group —$NR^{11}$— wherein $R^{11}$, $R^{14}$ and $R^{16}$ are as set forth above;

(v) $R^b$ and $R^c$ are each independently:

a reactive substituent; a compatiblizing substituent; hydrogen; hydroxy; $C_1$-$C_6$ alkyl; $C_3$-$C_7$ cycloalkyl; allyl; a substituted or unsubstituted phenyl or benzyl, wherein each of said phenyl and benzyl substituents is independently $C_1$-$C_6$ alkyl or $C_1$-$C_6$ alkoxy; halo; a substituted or unsubstituted amino; —C(O)$R^9$ wherein $R^9$ is hydrogen, hydroxy, $C_1$-$C_6$ alkyl, $C_1$-$C_6$ alkoxy, an unsubstituted, mono- or di-substituted phenyl or naphthyl wherein each of said substituents is independently $C_1$-$C_6$ alkyl or $C_1$-$C_6$ alkoxy, phenoxy, mono- or di-($C_1$-$C_6$)alkyl substituted phenoxy, mono- or di-($C_1$-$C_6$)alkoxy substituted phenoxy, amino, mono- or di-($C_1$-$C_6$)alkylamino, phenylamino, mono- or di-($C_1$-$C_6$)alkyl substituted phenylamino or mono- or di-($C_1$-$C_6$)alkoxy substituted phenylamino; —$OR^{18}$ wherein $R^{18}$ is $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ haloalkyl, allyl or —CH($R^{19}$)T wherein $R^{19}$ is hydrogen or $C_1$-$C_3$ alkyl, T is CN, $CF_3$ or $COOR^{20}$ wherein $R^{20}$ is hydrogen or $C_1$-$C_3$ alkyl, or wherein $R^{18}$ is —C(=O)U wherein U is hydrogen, $C_1$-$C_6$ alkyl, $C_1$-$C_6$ alkoxy, an unsubstituted, mono- or di-substituted phenyl or naphthyl, wherein each of said substituents are independently $C_1$-$C_6$ alkyl or $C_1$-$C_6$ alkoxy, phenoxy, mono- or di-($C_1$-$C_6$)alkyl substituted phenoxy, mono- or di-($C_1$-$C_6$)alkoxy substituted phenoxy, amino, mono- or di-($C_1$-$C_6$)alkylamino, phenylamino, mono- or di-($C_1$-$C_6$)alkyl substituted phenylamino or mono- or di-($C_1$-$C_6$) alkoxy substituted phenylamino; and a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_t$— or —[O—($CH_2$)$_t$]$_k$—, wherein t ranges from 2 to 6 and k ranges from 1 to 50, and wherein the substituent is connected to an aryl group on another photochromic material; or $R^b$ and $R^c$ together form an oxo group; provided that the 13-position of said indeno-fused naphthopyran is substantially free of spiro-substituents; and (vi) B and B' are each independently:

an aryl group that is mono-substituted with a reactive substituent or a compatiblizing substituent; an unsubstituted, mono-, di-, tri- or tetra-substituted aryl group; 9-julolidinyl; an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl; wherein the aryl and heteroaromatic substituents are each independently:

hydroxy, aryl, mono- or di-($C_1$-$C_{12}$)alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$) alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$) alkoxyaryl($C_1$-$C_{12}$)alkyl, mono- or di-($C_1$-$C_{12}$) alkylaryl($C_1$-$C_{12}$)alkoxy, mono- or di-($C_1$-$C_{12}$) alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy ($C_1$-$C_{12}$)alkyl, acryloxy, methacryloxy, halogen, or —C(=O)$R^{21}$ wherein $R^{21}$ is —$OR^{22}$, —N($R^{23}$)$R^{24}$, piperidino or morpholino, wherein $R^{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{23}$ and $R^{24}$ are each independently $C_1$-$C_6$ alkyl, $C_5$-$C_7$ cycloalkyl or a substituted or unsubstituted phenyl, said phenyl substituents independently being $C_1$-$C_6$ alkyl or $C_1$-$C_6$ alkoxy;

an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, said substituents being $C_1$-$C_{12}$ alkyl, $C_1$-$C_{12}$ alkoxy, phenyl or halogen; a mono-substituted phenyl, said phenyl having a substituent located at the para position, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_1$— or —[O—($CH_2$)$_t$]$_k$—, wherein t ranges form 2 to 6 and k ranges from 1 to 50, and wherein the substituent is connected to an aryl group on another photochromic material; a group represented by:

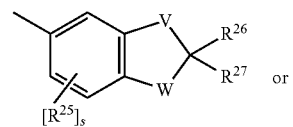

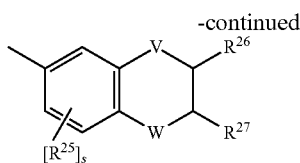

wherein V is —CH$_2$— or —O—, W is oxygen or substituted nitrogen, provided that when W is substituted nitrogen, V is —CH$_2$—, the substituted nitrogen substituents being hydrogen, C$_1$-C$_{12}$ alkyl or C$_1$-C$_{12}$ acyl, each R$^{25}$ independently being C$_1$-C$_{12}$ alkyl, C$_1$-C$_{12}$ alkoxy, hydroxy or halogen, R$^{26}$ and R$^{27}$ are each independently hydrogen or C$_1$-C$_{12}$ alkyl, and s ranges from 0 to 2; or a group represented by:

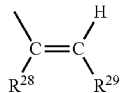

wherein R$^{28}$ is hydrogen or C$_1$-C$_{12}$ alkyl, and R$^{29}$ is an unsubstituted, mono- or di-substituted naphthyl, phenyl, furanyl or thienyl, said substituents being C$_1$-C$_{12}$ alkyl, C$_1$-C$_{12}$ alkoxy or halogen; or B and B' taken together form a fluoren-9-ylidene or mono- or di-substituted fluoren-9-ylidene, each of said fluoren-9-ylidene substituents independently being C$_1$-C$_{12}$ alkyl, C$_1$-C$_{12}$ alkoxy or halogen.

2. The photochromic material of claim 1, wherein the photochromic material comprises at least one of a reactive substituent and a compatiblizing substituent, each of said reactive substituent or compatiblizing substituent being independently represented by one of:

| -A'-D-E-G-J; | -G-E-G-J; | -D-E-G-J; |
| -A'-D-J; | -D-G-J; | -D-J; |
| -A'-G-J; | -G-J; and | -A'-J; | wherein:
(i) each -A'- is independently —O—, —C(═O)—, —CH$_2$—, —OC(═O)— or —NHC(═O)—, provided that if -A'- is —O—, -A'- forms at least one bond with -J;
(ii) each -D- is independently:
  (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue or an aromatic diamine residue, wherein a first amino nitrogen of said diamine residue forms a bond with -A'-, the group that extends the pi-conjugated system of the indeno-fused naphthopyran bonded at the 11-position thereof, or a substituent or an available position on the indeno-fused naphthopyran, and a second amino nitrogen of said diamine residue forms a bond with -E-, -G- or -J; or
  (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue or an aromatic amino alcohol residue, wherein an amino nitrogen of said amino alcohol residue forms a bond with -A'-, the group that extends the pi-conjugated system of the indeno-fused naphthopyran bonded at the 11-position thereof, or a substituent or an available position on the indeno-fused naphthopyran, and an alcohol oxygen of said amino alcohol residue forms a bond with -E-, -G- or -J, or said amino nitrogen of said amino alcohol residue forms a bond with -E-, -G- or -J, and said alcohol oxygen of said amino alcohol residue forms a bond with -A'-, the group that extends the pi-conjugated system of the indeno-fused naphthopyran bonded at the 11-position thereof, or a substituent or an available position on the indeno-fused naphthopyran;
(iii) each -E- is independently a dicarboxylic acid residue or a derivative thereof, said dicarboxylic acid residue being an aliphatic dicarboxylic acid residue, a cycloaliphatic dicarboxylic acid residue or an aromatic dicarboxylic acid residue, wherein a first carbonyl group of said dicarboxylic acid residue forms a bond with -G- or -D-, and a second carbonyl group of said dicarboxylic acid residue forms a bond with -G-;
(iv) each -G- is independently:
  (a) —[(OC$_2$H$_4$)$_x$(OC$_3$H$_6$)$_y$(OC$_4$H$_8$)$_z$]—O—, wherein x, y and z are each independently chosen and range from 0 to 50, and a sum of x, y, and z ranges from 1 to 50;
  (b) a polyol residue or a derivative thereof, said polyol residue being an aliphatic polyol residue, a cyclo aliphatic polyol residue or an aromatic polyol residue, wherein a first polyol oxygen of said polyol residue forms a bond with -A'-, -D-, -E-, the group that extends the pi-conjugated system of the indeno-fused naphthopyran bonded at the 11-position thereof, or a substituent or an available position on the indeno-fused naphthopyran, and a second polyol oxygen of said polyol forms a bond with -E- or -J; or
  (c) a combination thereof, wherein the first polyol oxygen of the polyol residue forms a bond with a group —[(OC$_2$H$_4$)$_x$(OC$_3$H$_6$)$_y$(OC$_4$H$_8$)$_z$]— and the second polyol oxygen forms a bond with -E- or -J; and
(v) each -J is independently:
  (a) a group —K, wherein —K is —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H or —SO$_3$H, wherein w ranges from 1 to 18;
  (b) hydrogen, provided that if -J is hydrogen, -J is bonded to an oxygen of -D- or -G-, or a nitrogen of -D-; or
  (c) a group -L or residue thereof, wherein -L is acryl, methacryl, crotyl, 2-(methacryloxy)ethylcarbamyl, 2-(methacryloxy)ethoxycarbonyl, 4-vinylphenyl, vinyl, 1-chlorovinyl or epoxy.

3. The photochromic material of claim 1, wherein at least one of an R$^e$ group at the 6-position, an R$^e$ group at the 7-position, B, B', R$^b$, R$^c$ and R$^a$ comprises a reactive substituent.

4. The photochromic material of claim 1 represented by graphic formula I wherein:
(i) each of an R$^e$ group at the 7-position and an R$^e$ group at the 6-position is independently —OR$^{10}$ wherein R$^{10}$ is C$_1$-C$_6$ alkyl, a substituted or unsubstituted phenyl, said phenyl substituents being C$_1$-C$_6$ alkyl or C$_1$-C$_6$ alkoxy, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, (C$_1$-C$_6$)alkoxy(C$_2$-C$_4$)alkyl, C$_3$-C$_7$ cycloalkyl or mono(C$_1$-C$_4$)alkyl substituted C$_3$-C$_7$ cycloalkyl; —N(R$^{11}$)R$^{12}$ wherein R$^{11}$ and R$^{12}$ are each independently hydrogen, C$_1$-C$_6$ alkyl, C$_1$-C$_6$ alkylaryl, C$_3$-C$_{20}$ cycloalkyl, C$_4$-C$_{20}$ bicycloalkyl, C$_5$-C$_{20}$ tricycloalkyl or C$_1$-C$_{20}$ alkoxyalkyl, wherein said aryl group is phenyl or naphthyl; a nitrogen containing ring represented by:

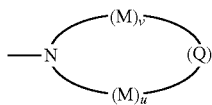

wherein each -M- is independently chosen for each occurrence from —CH$_2$—, —CH(R$^{13}$)—, —C(R$^{13}$)$_2$—, —CH(aryl)-, —C(aryl)$_2$- and —C(R$^{13}$)(aryl)-, and -Q- is -M-, —O—, —S—, —NH—, —N(R$^{13}$)— or —N(aryl)-, wherein each R$^{13}$ is independently C$_1$-C$_6$ alkyl, each (aryl) is independently phenyl or naphthyl, u ranges from 1 to 3, and v ranges from 0 to 3, provided that if v is 0, -Q- is -M-; or a reactive substituent or a compatiblizing substituent, provided that the reactive or compatiblizing substituent comprises a linking group comprising an aliphatic amino alcohol residue, a cyclo aliphatic amino alcohol residue, an azacyclo aliphatic alcohol residue, a diazacyclo aliphatic alcohol residue, a diamine residue, an aliphatic diamine residue, a cyclo aliphatic diamine residue, a diazacycloalkane residue, an azacyclo aliphatic amine residue, an oxyalkoxy group, an aliphatic polyol residue or a cyclo aliphatic polyol residue that forms a bond with the indeno[2',3':3,4]naphtho[1,2-b]pyran at the 6-position or the 7-position; or (ii) an R$^e$ group in the 6-position and an R$^e$ group in the 7-position of the indeno[2',3':3,4]naphtho[1,2-b]pyran together form a group represented by:

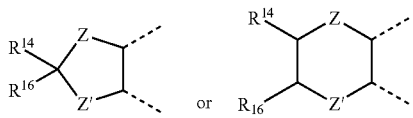

wherein Z and Z' are each independently oxygen or —NR$^{11}$—, wherein R$^{11}$ is as set forth above in (i).

5. The photochromic material of claim 1, wherein the photochromic material is chosen from: (i) a 3,3-di(4-methoxyphenyl)-6,7-dimethoxy-11-(4-trifluoromethyl)phenyl-13,13-dimethyl-3H,13H-indeno[2',3':3,4]naphtho[1,2-b]pyran; (ii) a 3,3-di(4-methoxyphenyl)-6,7-dimethoxy-11-(3,5-bis(trifluoromethyl))phenyl-13,13-dimethyl-3H,13H-indeno[2,1-f]naphtho[1,2-b]pyran; (iii) a 3,3-bis(4-methoxyphenyl)-6,7-dimethoxy-11-(2-trifluoromethyl)phenyl-13,13-diethyl-3H,13H-indeno[2',3':3,4]naphtho[1,2-b]pyran; (iv) a 3,3-di-(4-methoxyphenyl-6-methoxy-7-piperidino-11-(4-trifluoromethyl)phenyl-13,13-dimethyl-3H,13H-indeno[2,1-f]naphtho[1,2-b]pyran; (v) a 3-(4-methoxyphenyl)-3-(4-morpholinophenyl)-6,7-dimethoxy-1'-(4-trifluoromethyl)phenyl-13,13-dimethyl-3H,13H-indeno[2',3':3,4]naphtho[1,2-b]pyran; (vi) a 3-(4-methoxyphenyl)-3-(4-morpholinophenyl)-6-methoxy-7-piperidino-11-(4-trifluoromethyl)phenyl-13,13-dimethyl-3H,13H-indeno[2,1-f]naphtho[1,2-b]pyran; (vii) 3-(4-methoxyphenyl)-3-(4-morpholinophenyl)-6-methoxy-7-morpholino-11-(4-trifluoromethyl)phenyl-13,13-dimethyl-3H,13H-indeno[2,1-f]naphtho[1,2-b]pyran; (viii) 3,3-di(4-hydroxyphenyl)-6,7-dimethoxy-11-(3,5-bis(trifluoromethyl))phenyl-13,13-dimethyl-3H,13H-indeno[2,1-f]naphtho[1,2-b]pyran; (ix) 3,3-di-(4-methoxyphenyl-6-methoxy-7-morpholino-11-(4-trifluoromethyl)phenyl-13,13-dimethyl-3H,13H-indeno[2,1-f]naphtho[1,2-b]pyran; (x) 3,3-bis(4-methoxyphenyl)-6,7-dimethoxy-11-(2-trifluoromethyl)phenyl-13,13-dimethyl-3H,13H-indeno[2',3':3,4]naphtho[1,2-b]pyran; (xi) 3-phenyl-3'-(4-morpholinophenyl)-11-(4-trifluoromethyl)phenyl-13,13-dimethyl-3H,13H-indeno[2',3':3,4]naphtho[1,2-b]pyran; (xii) 3-(4-morpholinophenyl)-3-phenyl-11-(2-trifluoromethyl)phenyl-13,13-dimethyl-3H,13H-indeno[2',3':3,4]naphtho[1,2-b]pyran; (xiii) 3-(4-butoxyphenyl)-3-(4-methoxyphenyl)-6,7-dimethoxy-11-(3-(trifluoromethyl)pyridin-2-yl)-13,13-dimethyl-3H,13H-indeno[2',3':3,4]naphtho[1,2-b]pyran; and mixtures thereof.

6. A photochromic composition comprising the photochromic material of claim 1 incorporated into at least a portion of an organic material, said organic material being a polymeric material, an oligomeric material, a monomeric material or a mixture or combination thereof.

7. The photochromic composition of claim 6, wherein the organic material is a polymeric material, said polymeric material being poly(carbonate), a copolymer of ethylene and vinyl acetate; a copolymer of ethylene and vinyl alcohol; a copolymer of ethylene, vinyl acetate and vinyl alcohol; cellulose acetate butyrate; poly(urethane); poly(acrylate); poly(methacrylate); epoxy; an aminoplast functional polymer; poly(anhydride); poly(urea urethane); a N-alkoxymethyl (meth)acrylamide functional polymer; poly(siloxane); poly(silane); or a mixture or combination thereof.

8. The photochromic composition of claim 6, wherein the photochromic composition comprises at least one of a complementary photochromic material, a photoinitiator, a thermal initiator, a polymerization inhibitor, a solvent, a light stabilizer, a heat stabilizer, a mold release agent, a rheology control agent, a leveling agent, a free radical scavenger, and an adhesion promoter.

9. The photochromic composition of claim 6, wherein the photochromic composition is a coating composition.

10. An optical element comprising the photochromic material of claim 1.

11. The optical element of claim 10, wherein said optical element is adapted for use behind a substrate that blocks a substantial portion of electromagnetic radiation in the range of 320 nm to 390 nm, and further wherein at least a portion of said optical element absorbs at least a sufficient amount of electromagnetic radiation having a wavelength greater than 390 nm passing through said substrate that blocks said substantial portion of electromagnetic radiation in the range of 320 nm to 390 nm, such that at least a portion of said optical element transforms from a first state to a second state, wherein said first state of said optical element is a bleached state, and said second state of said optical element is a colored state.

* * * * *